United States Patent
Huang et al.

(10) Patent No.: US 11,738,208 B2
(45) Date of Patent: Aug. 29, 2023

(54) PARETO OPTIMAL PROJECTION SEARCH (POPS) FOR AUTOMATED RADIATION THERAPY TREATMENT PLANNING

(71) Applicant: The Board of Trustees of the Leland Stanford Junior University, Stanford, CA (US)

(72) Inventors: Charles Huang, San Diego, CA (US); Lei Xing, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 285 days.

(21) Appl. No.: 17/370,383

(22) Filed: Jul. 8, 2021

(65) Prior Publication Data

US 2022/0008748 A1    Jan. 13, 2022

Related U.S. Application Data

(60) Provisional application No. 63/049,315, filed on Jul. 8, 2020, provisional application No. 63/168,448, filed on Mar. 31, 2021.

(51) Int. Cl.
*A61N 5/10* (2006.01)

(52) U.S. Cl.
CPC ......... *A61N 5/1031* (2013.01); *A61N 5/1077* (2013.01)

(58) Field of Classification Search
CPC ........ A61N 5/10; A61N 5/103; A61N 5/1031; A61N 5/1077
USPC .......................................................... 378/65
See application file for complete search history.

(56) References Cited

U.S. PATENT DOCUMENTS

| 6,546,073 B1 * | 4/2003 | Lee ...................... A61N 5/1031 378/65 |
| 7,046,762 B2 * | 5/2006 | Lee ...................... A61N 5/1031 378/65 |
| 7,391,026 B2 * | 6/2008 | Trinkaus ................ G16H 70/20 378/65 |

(Continued)

OTHER PUBLICATIONS

C. Huang, Y. Yang, N. Panjwani, S. Boyd, and L. Xing, "Pareto Optimal Projection Search (POPS): Automated Radiation Therapy Treatment Planning by Direct Search of the Pareto Surface," in IEEE Transactions on Biomedical Engineering, vol. 68, No. 10, pp. 2907-2917, Oct. 2021. (Year: 2021).*

(Continued)

*Primary Examiner* — Allen C. Ho
(74) *Attorney, Agent, or Firm* — Lumen Patent Firm

(57) ABSTRACT

A method for radiation therapy treatment planning includes: a) defining a decision variable search space by projecting an initial seed point onto a pareto front, where the pareto front and decision variable search space are defined in the same coordinate space; b) projecting search points in the decision variable search space to the pareto front using a one-dimensional search algorithm to produce projected points on the pareto front; c) updating the search points by performing a gradient-free optimization that evaluates a treatment planning scoring function at the projected points on the pareto front; and d) repeating steps (b), (c) to search within the decision variable search space until a convergence criterion is satisfied, thereby producing a pareto optimal and clinically acceptable treatment plan.

4 Claims, 8 Drawing Sheets

(56) References Cited

U.S. PATENT DOCUMENTS

| | | | | |
|---|---|---|---|---|
| 7,876,882 | B2* | 1/2011 | Meyer | A61N 5/103 378/65 |
| 8,976,929 | B2* | 3/2015 | Wu | A61N 5/10 378/65 |
| 8,986,186 | B2* | 3/2015 | Zhang | A61N 5/103 600/1 |
| 9,507,886 | B2* | 11/2016 | Fiege | G06N 3/126 |
| 10,417,391 | B2* | 9/2019 | Teichert | A61N 5/1047 |
| 10,449,388 | B2* | 10/2019 | Yin | A61N 5/103 |
| 10,475,537 | B2* | 11/2019 | Purdie | G16H 50/20 |
| 10,549,121 | B2* | 2/2020 | Wu | A61N 5/1031 |
| 11,358,004 | B2* | 6/2022 | Wu | G16H 50/50 |
| 11,554,270 | B2* | 1/2023 | Andersson | A61N 5/1031 |

OTHER PUBLICATIONS

Breedveld et al., iCycle: Integrated, multicriterial beam angle, and profile optimization for generation of coplanar and noncoplanar IMRT plans, Med Phys. Feb. 2012;39(2):951-63.

Zarepisheh et al., Automated intensity modulated treatment planning: The expedited constrained hierarchical optimization (ECHO) system. Med Phys., Jul. 2019;46(7):2944-2954.

Papp et al., A modular approach to intensity-modulated arc therapy optimization with noncoplanar trajectories. 2015 Phys. Med. Biol. vol. 60 No. 13, 5179.

Huang et al., Pareto Optimal Projection Search (POPS): Automated Radiation Therapy Treatment Planning by Direct Search of the Pareto Surface. IEEE Trans Biomed Eng. Feb. 1, 2021.

Huang et al., Fully Automated Noncoplanar Radiation Therapy Treatment Planning, arXiv:2104.00784 [physics.med-ph], [v1] Thu, Apr. 1, 2021.

* cited by examiner

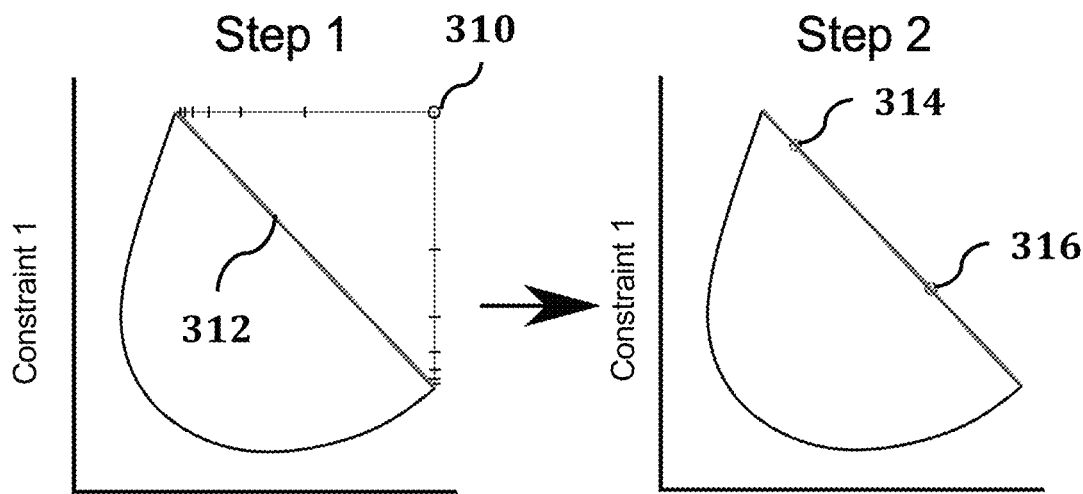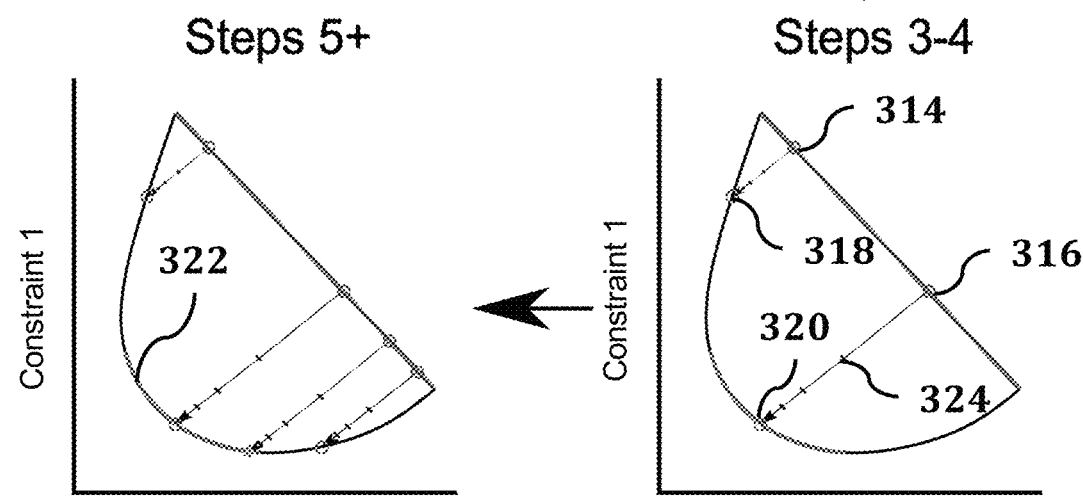
Fig. 3B  Fig. 3C  Fig. 3D  Fig. 3E

PARETO OPTIMAL PROJECTION SEARCH (POPS) FOR AUTOMATED RADIATION THERAPY TREATMENT PLANNING

CROSS-REFERENCE TO RELATED APPLICATIONS

This application claims priority from U.S. Provisional Patent Application 63/049,315 filed Jul. 8, 2020, which is incorporated herein by reference. This application claims priority from U.S. Provisional Patent Application 63/168,448 filed Mar. 31, 2021, which is incorporated herein by reference.

STATEMENT OF FEDERALLY SPONSORED RESEARCH

This invention was made with Government support under contract EB009653 awarded by the National Institutes of Health, under contract CA227713 awarded by the National Institutes of Health, and under contract CA176553 awarded by the National Institutes of Health. The Government has certain rights in the invention.

FIELD OF THE INVENTION

The present invention relates generally to techniques for radiation therapy treatment planning. More specifically, it relates to techniques for automatically finding treatment plan solutions.

BACKGROUND OF THE INVENTION

Radiation therapy treatment planning involves determination of a plan for the delivery of a prescribed radiation dose to a target volume (i.e. tumor volume) while minimizing dose to surrounding organs-at-risk (OARs). Towards this overall goal, an iterative process called treatment planning is performed in order to find a treatment plan solution that is both pareto optimal and clinically acceptable. Treatment planning iterative adjustments are conventionally performed manually by physicians, making the process notoriously time-consuming and labor intensive, with no guarantee that a good solution is found.

SUMMARY OF THE INVENTION

Here we disclose a technique for radiation treatment planning employing a pareto optimal projection search (POPS), which automates the treatment planning process and converges to treatment plan solutions that are pareto optimal and clinically acceptable. POPS can automate the treatment planning component of radiation therapy for any treatment planning system, all in under approximately 60 minutes on mid-level consumer desktop hardware (which can be sped up with a faster inverse planning solver or better computer hardware). The technique does not depend on specific treatment planning hardware or software and can, therefore, be incorporated into any commercial or open-source treatment planning package. Essentially, any hospitals performing radiation therapy, any of over 20 manufacturers providing hardware and software solutions for these hospitals, and millions of cancer patients should benefit from this technique.

Treatment planning is an iterative process that involves the adjustment of various treatment planning parameters with the purpose of arriving at a pareto optimal and clinically acceptable treatment plan. For a treatment plan to be pareto optimal, improvements to the plan in regards to one criterion (e.g., less dose to a particular organ at risk) can only be made by trading off in regards to at least another criterion (e.g., less uniform dose delivered to the target). Clinical acceptability for treatment plans is typically a qualitative determination based on the judgment and expertise of physicians. The POPS technique automates the treatment planning process by generating treatment plan solutions that are both pareto optimal and clinically acceptable.

The key idea of the proposed POPS technique is to search the Pareto front for desirable treatment plan solutions, as defined by a scoring function that mimics the decision-making process of manual planning. The POPS approach has two main components: 1) gradient-free search of the relevant dose constraint bounds (search points) and 2) projection of search points to the Pareto front. The full POPS algorithm, various scoring functions, and an extension of the POPS algorithm using beam angle optimization is described later in detail.

The POPS technique can be integrated into any existing treatment planning system (software and hardware). Due to the system-agnostic nature of the POPS approach, any potential treatment planning system (whether deployed now or in the future) could benefit from this approach. Current workflows for treatment planning heavily involve physicians and lockup valuable physician time that could be spent better elsewhere. The POPS technique automates the treatment planning process and relieves physicians of that burden, allowing for potentially drastic improvements in patient turnover and overall quality of care. POPS may be used by companies producing treatment planning systems and software, hospitals in need of automating their treatment planning workflow, physicians performing iterative treatment planning, as well as other researchers.

Advantages and improvements over existing methods include the following: The POPS technique can automate the treatment planning process and is robust to changes in plan configuration, patient geometry, etc. To the best of our knowledge, the POPS technique is the only practically feasible automated approach to producing pareto optimal and clinically acceptable treatment plans, while utilizing inverse planning directly. Other existing approaches such as a posteriori multi-criteria is optimization rely on slow database generation that becomes infeasible as problem complexity increases (more structures/OARs) and can take on the order of years to completely search the treatment plan solution space. In contrast, our methods converge to the best pareto optimal solution in approximately 60 minutes (which can be sped up with a faster inverse planning solver or better computer hardware).

In one implementation, the feasibility search involves iteratively adjusting the equivalent uniform dose (EUD) constraint values for various organs-at-risk (OARs), but the POPS technique in general can be applied to any feasibility search problem setup. Examples of other feasibility search setups may include replacement of the EUD constraints with other constraints (e.g. min/max constraints, mean constraints, DVH constraints, etc.) or replacement of the squared objective.

The POPS technique can be advantageously applied to providing a solution to automating noncoplanar treatment planning problems by extending the Pareto-Optimal Projection Search (POPS) to the noncoplanar setting. Typically, clinical treatment planning deals with coplanar beams and arc trajectories. Noncoplanar beams and arcs, however, have tremendous potential to improve dosimetric quality of plans.

Noncoplanar treatment plans can achieve better sparing for organs-at-risk (OARs) than traditional coplanar plans. Here we disclose combining POPS with iterative beam angle optimization (BAO) to provide a framework for fully automated noncoplanar treatment planning. This combination includes 1) beam angle optimization using combinatorial optimization (CO) and 2) fully automated inverse planning using the Pareto Optimal Projection Search (POPS) algorithm.

This combination of POPS with BAO includes a series of related techniques for station parameter optimized radiation therapy (SPORT) treatment planning. Briefly, a station control point (or node or control point) describes the state of LINAC delivery system (including LINAC configurations such as beam energy, aperture shape and weight, gantry/collimator angle, isocenter, and auxiliaries such as the couch). A conventional intensity modulated beam has a collection of stations with the same gantry angle but different MLC and MU settings. VMAT and IMRT are simply two special cases of SPORT.

First, we propose an iterative algorithm for SPORT beam angle optimization (BAO), or the process of finding optimal beam directions. This iterative approach produces an ensemble of promising beam directions or station points to be used for noncoplanar IMRT planning. For noncoplanar VMAT, these beam station points are then converted to dynamic trajectories by solving a shortest path problem between beam control points. Second, given a set of beam control points or dynamic trajectories, fully automated inverse planning can be performed by applying the POPS technique.

The BAO process is formulated as a combinatorial optimization problem. In this formulation, we attempt to create an ensemble of promising beam directions by iteratively adding beams (couch and gantry angle pairs) from the candidate set of feasible beams. Next, an iterative approach is adopted to select promising beam angles. In each iteration, we compute the utility of each feasible beam angle as defined by a convex multi-objective function (i.e. EUD, quadratic objectives, etc.). This objective function can include terms for the target, OARs, and other plan considerations like dose conformity. Following an iterative approach, we then select the beam angle which provides the global minimum objective function value and add that beam angle to the ensemble. In subsequent iterations, we compute the objective function values for each beam in the feasible set again, and we then select the global minimum beam angle. This iterative approach is repeated until the beam ensemble contains the desired number of beams. The BAO process is completed once the ensemble of promising beam directions has been created. From there, inverse planning is done using POPS.

In one aspect, the invention provides a method for radiation therapy treatment planning, the method comprising: a) defining a decision variable search space by projecting an initial seed point onto a pareto front, where the pareto front and decision variable search space are defined in the same coordinate space; b) projecting search points in the decision variable search space to the pareto front using a one-dimensional search algorithm to produce projected points on the pareto front; c) updating the search points by performing a gradient-free optimization that evaluates a treatment planning scoring function at the projected points on the pareto front; d) repeating steps (b), (c) to search within the decision variable search space until a convergence criterion is satisfied, thereby producing a pareto optimal and clinically acceptable treatment plan.

The method may further comprise performing beam angle optimization using combinatorial (joint) optimization. The beam angle optimization may be non-coplanar or coplanar.

BRIEF DESCRIPTION OF THE DRAWINGS

FIGS. 3B-3D illustrate the steps of the steps of an embodiment of the invention separately, where FIG. 3B shows a seed point defining a decision variable space, FIG. 3C shows initial search points in decision space, FIG. 3D shows projection of the search points to the Pareto front, and FIG. 3E shows how a gradient-free search of the Pareto front is used to find a clinically acceptable treatment plan.

DETAILED DESCRIPTION OF THE INVENTION

Figure 1:
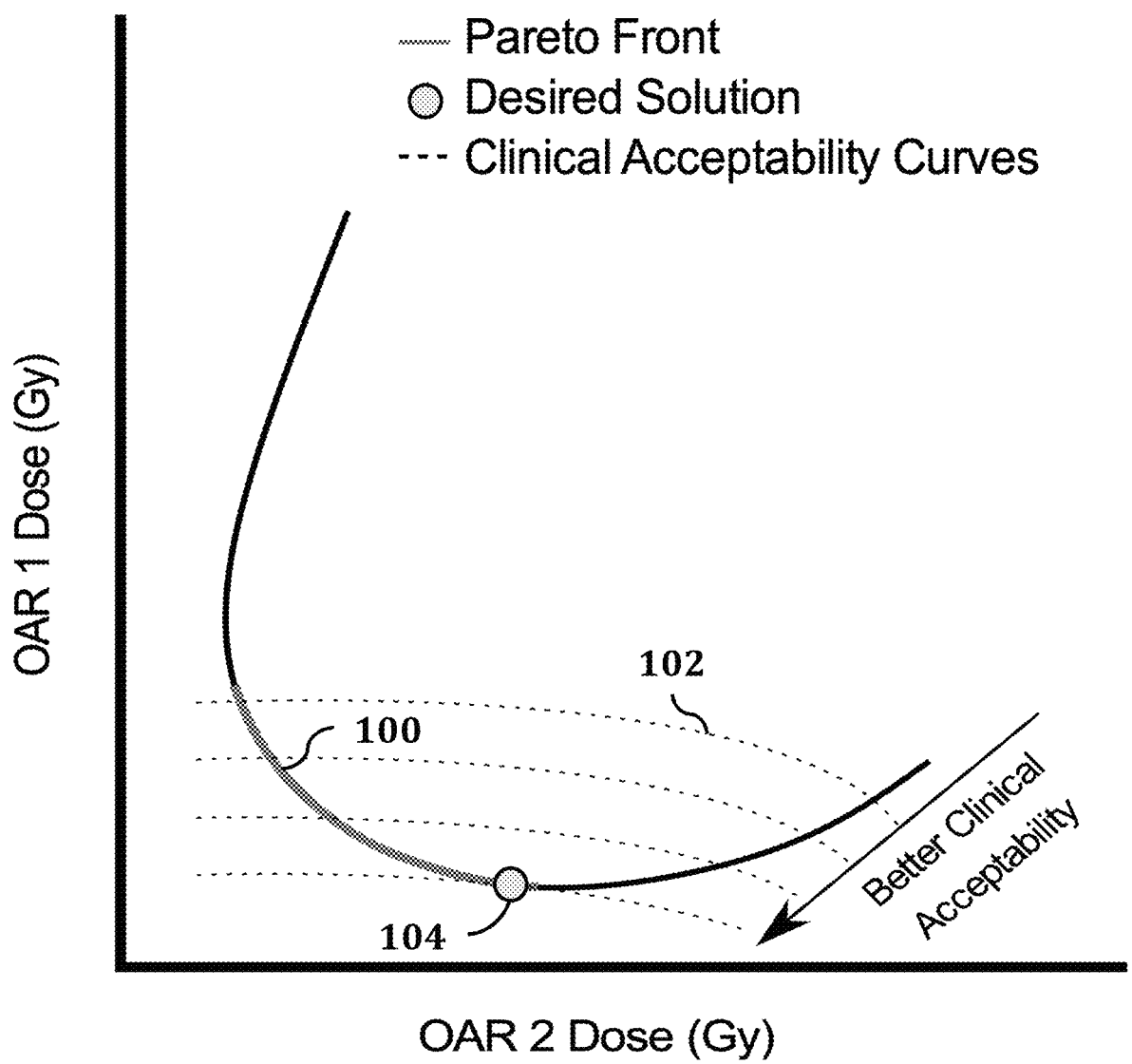
FIG. 1 is a graph that illustrates features of a decision-making process of human planners for selecting Pareto optimal plans based on improving clinical acceptability, showing a Pareto front curve, clinically acceptability curves, and desired treatment plan solution, graphed in a space spanned by different optimization variables (criteria), OAR 1 Dose (Gx) and OAR 2 Dose (Gy).

External beam radiation therapy involves the delivery of ionizing radiation with the intent to treat diseased tissue while minimizing dose to healthy organs [1], [2]. The goal of treatment planning is then to determine optimal beam angles, shapes, intensities, etc. that satisfy this overall clinical objective. Oftentimes, the treatment planning process represents a bottleneck to high quality patient care, due to the time-consuming nature of the iterative planning process and inter-planner variability.

Prior to treatment, medical images are collected for the patient (e.g. CT, MRI, or PET scans), and physicians contour various anatomical structures on the collected images, including the planning target volume (PTV) and surrounding organs-at-risk (OARs) [3], [4]. For the case of intensity modulated radiation therapy (IMRT), planners determine the appropriate plan configuration (i.e. beam type, beam angle arrangement, etc.) and perform inverse planning to achieve a desired dose distribution or to satisfy various objectives and constraints [3], [4]. Many of these same principles are also used in the case of volumetric modulated arc therapy (VMAT) [5] and have been shown to improve delivery efficiency while maintaining or improving dosimetric quality[6]-[11].

Traditionally, treatment planning has been a manual, iterative process to be performed by human planners. In this process, planners repeatedly adjust treatment planning parameters (TPPs), such as objective weights, dose constraint values, etc., until a clinically acceptable treatment plan solution is found. The iterative planning process is not only time-consuming and labour intensive, but the resulting plan quality highly depends on planner skill and experience [12]-[19]. Automated methods, therefore, aim to reduce active planning time (with fully automated methods requiring no active planning).

In radiation therapy inverse planning, translating clinical goals into a multicriteria objective function for optimization is often very difficult [19]. In developing automated methods for treatment planning, there are three main considerations: (1) to reduce active planning time, (2) to produce acceptable plans that satisfy clinical criteria, and (3) to produce plans that are efficient.

From a design perspective, leaving performance on the table is highly undesirable. As treatment planning can involve many conflicting objectives (e.g. reduce mean OAR doses, minimize the deviation in PTV dose from the prescribed dose, etc.), no single plan can optimize performance on all objectives at once. The treatment planning problem can instead be approached using multicriteria optimization, with the goal of producing Pareto optimal, nondominated solutions. These Pareto optimal plans are efficient—that is we cannot improve one aspect (e.g., reduce the dose in one OAR) without compromising at least one other aspect (e.g., reduce the PTV dose) [20], [21]. Plans that are not Pareto optimal (i.e. dominated plans) are inefficient, and there exists more optimal plan(s) that, for instance, achieve better organ sparing for all OARs.

Pareto optimal planning enables planners to produce efficient treatment plans that can leverage a treatment planning system (TPS) configuration to the best of its abilities. Intuitively, producing efficient plans is a cornerstone of high-quality patient care, but not all Pareto optimal plans are acceptable clinically.

FIG. 1 shows a Pareto front curve, clinically acceptability curves, and desired treatment plan solution, graphed in a space spanned by different optimization variables (criteria), OAR 1 Dose (Gx) and OAR 2 Dose (Gy). This illustrates a decision-making process of human planners for selecting Pareto optimal plans based on improving clinical acceptability. Here, the curve 100 represents the Pareto front, where not all plans are equally clinically acceptable. The clinical acceptability curves are shown as dotted curves 102. The decision-making process of a planner might be conceptualized as selecting Pareto optimal plans, such as solution plan 104, that appear most appealing or clinically acceptable [21]. The methods of the present invention use techniques to automate this decision-making process and produce treatment plans that are both Pareto optimal and clinically acceptable.

In general, strategies of automating treatment planning can be categorized as knowledge-based planning (KBP) [23]-[26], protocol-based planning (PBP)[13], [14], [27]-[30], and multicriteria optimization (MCO) [12], [20], [31]-[35]. As each category of approaches has its own benefits and drawbacks, no clear consensus has been reached on an approach that can completely replace manual planning, and, in practice, a combination of various approaches may be used in a case-by-case fashion.

KBP methods are a category of methods based on the premise that treatment planning results can be predicted from the geometric and anatomical information of a patient [23]. KBP typically follows the paradigm of training a supervised machine learning model on a dataset of previously generated treatment plans. Given input information in the form of a patient's CT and structure segmentations, a knowledge-based model attempts to predict voxel-wise dose or the dose-volume histogram (DVH) [23]-[26]. Previous works report that knowledge-based models can accurately predict treatment planning results [23]-[25], but these results are often limited to a subset of the information in treatment plans (i.e. dose distribution, DVH, etc.) and are not equivalent to performing the treatment planning process. In cases where KBP performs poorly, lack of model interpretability limits the usability of KBP approaches. Moreover, because KBP is typically formulated as a supervised learning problem, it makes no guarantees about the efficiency of produced plans and, instead, only attempts to produce plans that are similar to the ground-truth data used in training, which may be a limiting factor on algorithm performance. Combined, these drawbacks may limit the practical usability of KBP methods in the clinic, at least in their present forms [55].

PBP methods are a category of methods that employ rules or heuristics to mimic an experienced treatment planner performing iterative planning. Previous works have proposed various rules for adjusting treatment planning parameters (i.e. objective weights, constraint values, etc.) based on advice from consulted physicians [14], [27]-[30]. Others have followed a model-free approach, opting to use reinforcement learning to mimic human planners [13].

While protocol-based methods may offer a practical approach to automation, they do not directly address the issue of inter-planner variability. In particular, the design of rules or heuristics for protocol-based planning highly depends on the perspective of the planner, leading to variable plan quality between institutions or even individual planners [14], [15]. Automated approaches, ideally, should remove inter-planner variability and provide a baseline method for producing high-quality treatment plans, but the issue of inter-planner variability remains very present in protocol-based approaches.

Unlike KBP and PBP approaches, MCO approaches attempt to generate Pareto optimal treatment plans. MCO approaches can be further categorized into a posteriori MCO [20], [31], [32] and a priori MCO [12], [33], [34].

In a priori MCO, a Pareto optimal solution is found according to provided preferences [19], [51]. Such approaches require sufficient preference information to be provided by the planner, and some notable examples include scalarization (e.g. ϵ—constraint method, achievement scalarization, etc.) [52], prioritized optimization [12], [33], [34], and the lexicographic method [53]. Translating physicians' intuitions regarding ideal planning to a list of preferences, however, is no trivial task, and sometimes treatment plan solutions found from preference information may not align with a planner's expectations. Where preference information may only capture general trends observed by a physician, more nuanced metrics that utilize dose-volume histogram information is likely necessary.

A posteriori MCO, by contrast, explicitly place the decision of selecting treatment plans in the hands of the planner. These methods attempt to generate or approximate the Pareto surface, creating a database of Pareto optimal treatment plans that a physician might choose from. Previous works have proposed alternative ways to generate the Pareto surface (e.g. Pareto surface generation for convex multiobjective instances or PGEN, simulated annealing, evolutionary algorithms, etc.) or at least approximate its shape assuming a convex formulation to the problem [20], [31], [32]. A posteriori methods, in general, produce Pareto optimal and clinically acceptable plans, though at high computational cost. Further, these methods still require physicians to select clinically acceptable plans from the generated database and, therefore, are not fully automated methods.

Methods

The fully automated Pareto Optimal Projection Search (POPS) technique directly searches the Pareto front for clinically acceptable plans, doing so in a fully automatic fashion. POPS produces Pareto optimal plans, ideally, without the limitations of a priori and a posteriori methods. Instead of a list of preferences based on general trends, POPS uses a detailed scoring function to evaluate plans on clinical acceptability. POPS additionally performs an automated search using such a scoring function, and, in theory, does not require any active planning from human planners as is necessary for a posteriori methods. Our results demonstrate that POPS indeed produces Pareto optimal treatment plans that perform at least as well as dosimetrist is generated plans in terms of clinical acceptability.

Problem Formulation

The purpose of our fully automated POPS technique is two-fold: to produce treatment plans that are both Pareto optimal and optimal with respect to clinical acceptability. On one hand, alternative automated approaches like KBP and PBP do not directly address the issue of generating efficient plans. Alternative MCO approaches, on the other hand, discuss methods for generating the Pareto front while delegating the task of selecting the acceptable plan to a human planner. The present approach further reduces active planning times for MCO methods by directly searching the Pareto front for clinically acceptable plans, producing plans that are both Pareto optimal and clinically acceptable.

As previously mentioned, Pareto optimal plans are non-dominated and further improvements to the plan in regards to one aspect are only made by trading-off in regards to other aspects. Intuitively, Pareto optimal treatment plans lie on the front between the region of feasible and infeasible plans. As described previously, one valid way of formulating the problem is to perform multicriteria optimization with multiple weighted objective functions. Such an approach, however, involves a separate decision space and objective function space, which contains the Pareto front.

Figure 2A:
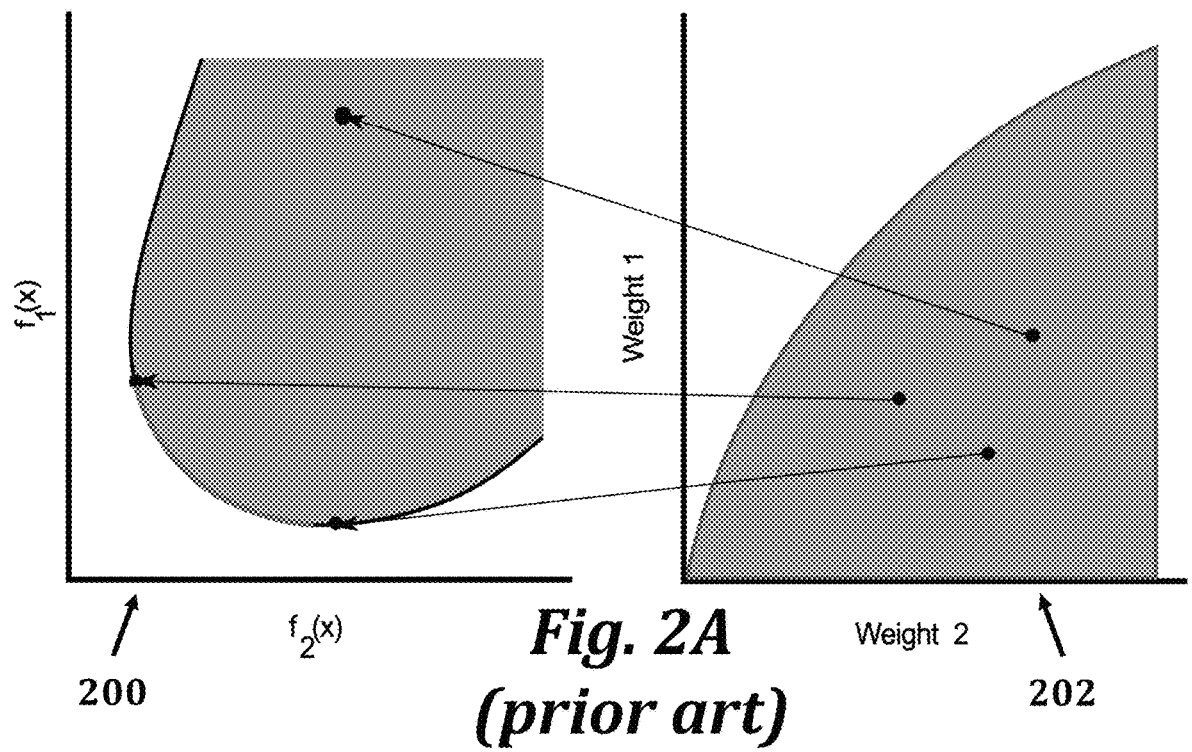
FIG. 2A illustrates two separate spaces used for traditional weighted optimization is problem setups: decision variable space and objective function space.
Figure 2B:
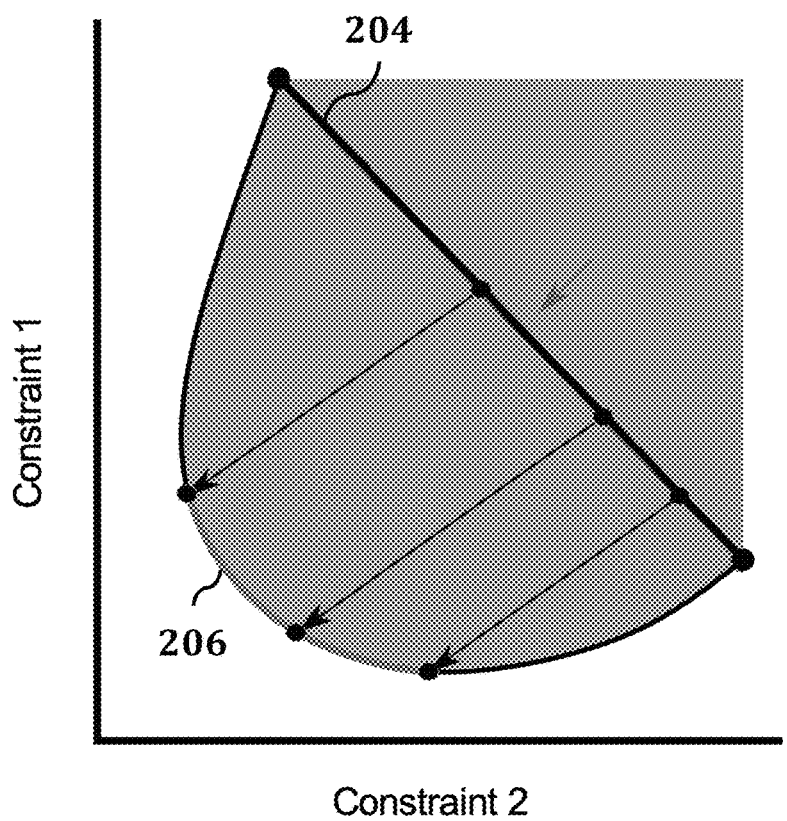
FIG. 2B illustrates the direct projections of points in the decision variable space to the Pareto front, according to an embodiment of the invention.

FIG. 2A illustrates the separate decision variable space 202 and objective function space 200 for traditional weighted optimization problem setups. Because the decision variables (i.e. objective weights) in MCO do not typically have an intuitive mapping to the objectives, many MCO methods focus primarily on generating the Pareto front. In contrast, the POPS technique instead formulates the iterative treatment planning problem as a feasibility search, which allows for a more direct relationship (projection) between the decision and constraint feasibility spaces. FIG. 2B illustrates the direct projections between the decision variable space 204 and the Pareto front 206 for POPS. The shaded area represents feasible plans in the constraint space. In brief, points from the decision variable space are projected to the constraint feasibility space, and then any gradient-free searching algorithm is used to navigate to a desired treatment plan solution. Both the decision space and Pareto front are represented in the same constraint space, allowing such a projection to be performed in a straightforward manner.

Quantifying Clinical Acceptability

Traditionally, the evaluation of treatment plans has been a manual, iterative, and qualitative process. In performing their qualitative evaluation, physicians ideally draw on their repository of clinical experience to judge various components of the plan. Previous works that explore various DVH constraints have attempted to operationalize the considerations made in a physician's qualitative assessment [18], [19], [36], [37]. Similarly, evaluation of treatment plans through various metrics has been used previously in knowledge based planning [23]-[25], as well as more broadly for data analytics [18], [36], [37].

To summarize the general intuition that can be followed in quantifying clinical acceptability of treatment plans, the overall quality of a treatment plan can be determined by assessing its performance in regards to individual metrics and criteria. We can first define a list of criteria, termed clinical acceptability criteria, that a physician might incorporate into their evaluation. As a foundation for our proposed list, we incorporate criteria from the list of DVH constraints discussed in Chen et al.[38]. While this particular list of criteria may not be agreeable to every physician, the entries can be readily changed to suit individual preferences or to follow various institutional protocol. Essentially each criterion represents a chosen control point on the DVH, and while we use in this example the control points identified in Chen et al., other control points may certainly be used to similar effect. The main heuristic we follow in selecting these criteria is to provide relatively uniform sampling to the DVH for each organ. Based on advice from three consulted physicians and our uniform sampling heuristic, we then incorporate additional criteria to judge sparing of the body, separate from sparing of surrounding OARs. The full list of criteria is included in Table 1. Here, D(•%) refers to dose at a given percent volume, D(max) refers to the maximum dose, and $D_p$ refers to the prescription dose. Each criterion can be conceptualized as a bound on the dose received by a certain OAR volume. The first rectum criteria (D(80%)≤30) could be understood as "the dose received by 80% of the volume should be at most 30 Gy."

TABLE 1

List of clinical acceptability criteria used in scoring prostate patients, the priority of each OAR, and the alpha values for the piece-wise sigmoid function. Dose values are in units of Gy.

| | Clinical Acceptability Criteria | Priority | $\alpha_1$ | $\alpha_2$ |
|---|---|---|---|---|
| Rectum | D(80%) ≤30 | 2 | 0.2 | 3 |
| | D(55%) ≤47 | | | |
| | D(40%) ≤65 | | | |
| | D(25%) ≤70 | | | |
| | D(10%) ≤75 | | | |
| | D(max) ≤1.1 $D_p$ | | | |
| Bladder | D(80%) ≤30 | 3 | 0.2 | 3 |
| | D(55%) ≤47 | | | |
| | D(30%) ≤70 | | | |
| | D(max) ≤1.1 $D_p$ | | | |
| Right Femoral Head | D(max) ≤50 | 4 | 0.2 | 3 |
| Left Femoral Head | D(max) ≤50 | 4 | 0.2 | 3 |
| Body | D(20%) ≤8 | 5 | 0.2 | 3 |
| | D(15%) ≤15 | | | |
| | D(10%) ≤25 | | | |
| | D(max) ≤1.1 $D_p$ | | | |

From a list of criteria, we can then design individual scoring functions ideally tailored to the criteria and structure being judged. Previous works have proposed a variety of scoring functions [18], [36], [37], [39]. Some of these scoring functions (e.g. step function, regret, etc.) are too broad and lack organ-specific considerations [18], [37].

Others, like the generalized evaluation metric (GEM) [36], attempt to incorporate organ-specific scoring at the cost of maintaining a lengthy history of treatment plan solutions. As defined in the GEM score, organ-specific scoring is represented by a gamma distribution probability term. To maintain an accurate gamma distribution, the GEM score requires a lengthy history of treatment plans. However, it is preferable to maintain organ-specific scoring without requiring a lengthy history, so we modify the previously proposed GEM score by replacing its gamma distribution probability term with piece-wise sigmoid functions. Like the original GEM score, our scoring function (SF) outputs a value between 0 and 1 (lower is better) where a score of 0.5 represents a plan that satisfies all clinical acceptability criteria, on average.

As shown in Equations 1 and 2, the intuition of organ-specific scoring is encapsulated by tailored piece-wise sigmoid functions (where $\alpha_1$ and $\alpha_2$ describe the steepness of the sigmoid functions and are chosen empirically) and a priority-based weighting (where the weighting scheme is adapted from Mayo et al. [36]).

$$SF = \begin{cases} 1, & \text{if solution is infeasible} \\ \frac{\sum_{s \in S} 2^{-Priority_s + 1} \cdot \frac{\sum_{i \in S} \sigma_i^{\pm}(PV_i - CV_i, \alpha_1, \alpha_2)}{N_s}}{\sum_{s \in S} 2^{-Priority_s + 1}}, & \text{otherwise} \end{cases} \quad (1)$$

$$\sigma_i^{\pm}(z_i, \alpha_1, \alpha_2) = \begin{cases} \frac{1}{1 + e^{-\alpha_1 z}}, & z \leq 0 \\ \frac{1}{1 + e^{-\alpha_2 z}}, & z > 0 \end{cases} \quad (2)$$

To select the steepness of the sigmoid functions, we adhere to the following heuristics:

1. Decreasing DVH values for each organ imply better sparing to that organ
2. Organ doses approaching 0 have diminishing returns, in regards to score
3. Not satisfying the listed clinical acceptability criteria is highly undesirable and intuitively results in a bad score Following these heuristics, $\alpha_1$ is selected to be small in order to abide by heuristic 2 and $\alpha_2$ is selected to be large relative to $\alpha_1$ in order to abide by heuristic 3. $\alpha_1, \alpha_2 \in (0, \infty)$, and $\alpha$ values on the lower and upper ends of that interval can be interpreted as the sigmoid function being a flat line and step function, respectively. Priority values for each OAR were selected based on advice from three consulted physicians.

Following the precedent of Mayo et al.[36], our clinical acceptability criteria do not include the target volume. For prostate IMRT, where the target volume is relatively large and the dose distribution to the target is relatively homogeneous (at least for the dose constraints used here), inclusion of target volume clinical acceptability criteria may be unnecessary. For other regions of the body or in particularly complex treatment planning cases, target volume criteria can certainly be incorporated without affecting POPS performance.

In Equation 2, s refers to a structure (OAR) in the structure set S. The priority of a specific structure, $Priority_s$, adjusts its exponential weighting. i refers to a clinical acceptability criteria (as listed in Table 1), $N_s$ refers to the total number of clinical acceptability criteria for a specific structure, and $\sigma^{\pm}$ refers to the structure score computed using a piecewise sigmoid function of the difference between the plan value $PV_i$ and the criteria value $CV_i$.

As an example, to compute the structure score for the second bladder criteria (D(55%)≤47), we first compute the difference $z_i = PV_i - CV_i$. Here, $CV_i = 47$ Gy and $PV_i$ is found as the corresponding dose on the bladder DVH for 55% volume. In this toy example, we use a plan value $PV_i = 20$ Gy, $\alpha_1 = 0.2$, and $\alpha_2 = 3$. We would then compute the structure score $\sigma_i^{\pm}(z_i, \alpha_1, \alpha_2) = 0.0045$. Assuming the solution is feasible, the scoring function then performs a weighted-average using OAR priorities. Our results use the priorities as listed in Table 1, which were determined based on advice from three consulted physicians, but they may also be changed to better suit individual planner preferences.

Intuitively, our SF scores treatment plans on a scale between 0 and 1, where lower scores are better. Plans that attain scores of 0.5 satisfy the listed clinical acceptability criteria, on average. Plans that attain scores smaller than 0.5 achieve better OAR sparing, on average, than a plan that just satisfies the listed clinical acceptability criteria.

POPS Technique

The general methodology of the POPS technique combines two search methodologies: 1) a projection from the decision variable space to the Pareto front using the bisection method [40] and 2) a gradient-free search (i.e. simplex search) of the decision variable space—and the corresponding points on the Pareto front—for a clinically acceptable treatment plan. In one implementation we use Nelder-Mead simplex search [41] due to its simplicity, but our methods can incorporate any gradient-free optimization approach. To allow for better reproducibility of our results, we implement our approach using the open-source MatRad software package [4].

Seed Point Selection

To start, we first select a seed point, which will later be used to bound the decision variable search space. Seed point selection varies with the treatment region (e.g. prostate, head and neck, lung, etc.), as each region has differing OARs each with differing dose constraints.

For our experiments on prostate cases, we chose to set the seed point coordinate to the maximum allowed EUD value of each OAR. Setting the seed point too small can cause the algorithm to miss portions of the Pareto front, as they will be outside the bounds of the decision variable search space. Conversely, setting the seed point arbitrarily large would lead to longer computation times, as the bisection method will need to be run over more iterations to project points to the Pareto front.

Projection Method

Figure 3A:
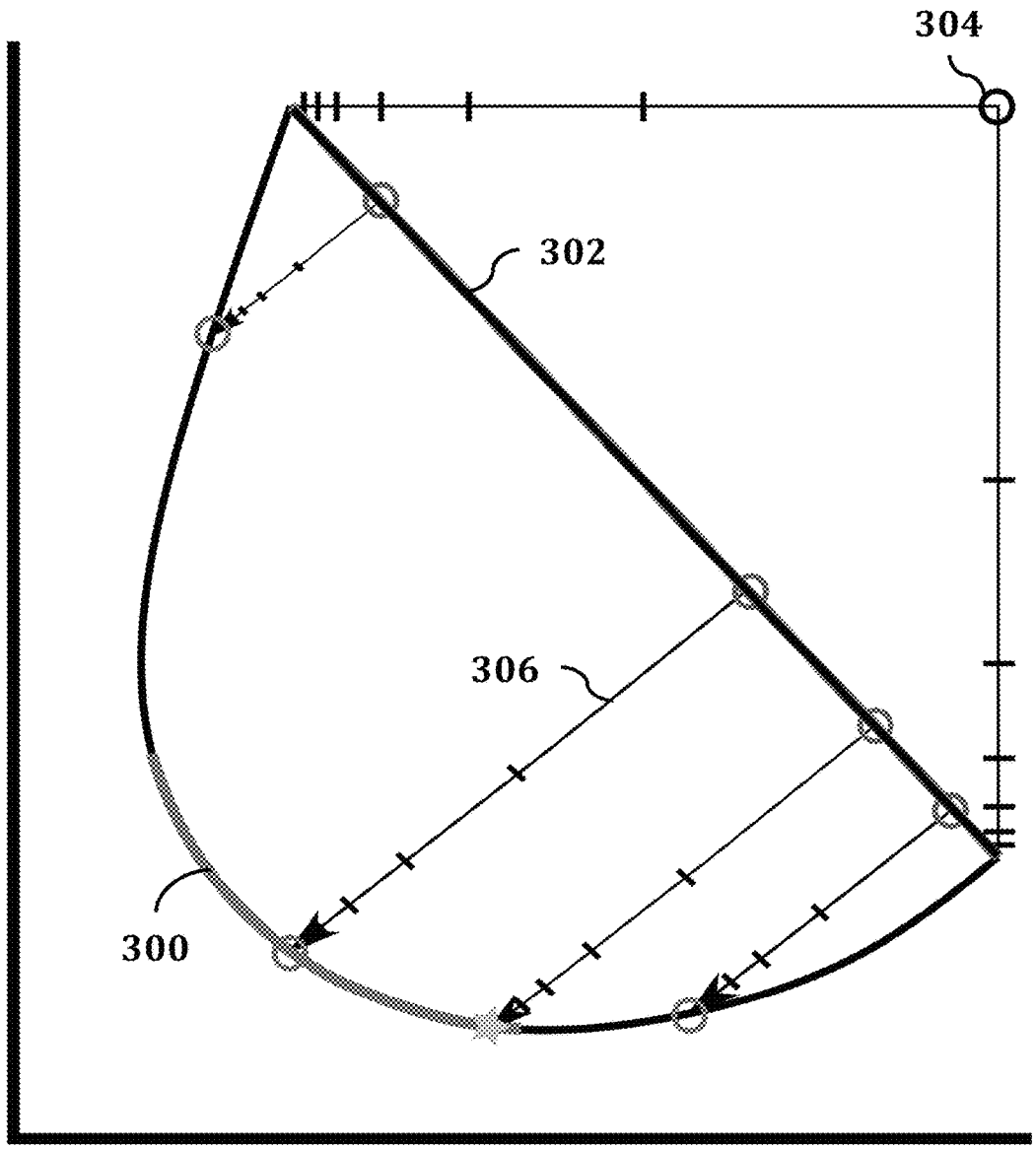
FIG. 3A is a visualization in constraint space of aspects technique of an embodiment of the invention, showing a seed point, a decision variable space, and points in the decision variable space being projected to the Pareto front.

In conventional MCO approaches with weighted optimization, the decision variable search space (i.e. objective weights) and Pareto front can be present in separate spaces (see FIG. 2A). Whereas in the POPS feasibility search problem, we define the decision variable search space and the Pareto front to be in the same coordinate space (see FIG. 2B). In doing so, we can also define a mapping between each point in the decision variable search space and a corresponding point on the feasibility boundary by conducting a feasibility search using the bisection method. For conciseness, we can refer to this feasibility search as a projection of points in the decision variable search space to the feasibility boundary. FIG. 3A is a visualization of aspects of the POPS technique for a hypothetical 2D problem. The figures shows the seed point 304, the decision variable space 302, the Pareto front 300 and the projection 306 from a point in the decision space to a corresponding point in the Pareto front.

FIGS. 3B-3D illustrate the steps of the method separately. In FIG. 3B, starting from a seed point 310, we define the bounds for the decision variable space 312 by projecting the seed point using the bisection method. In FIG. 3C, we then define the initial simplex by its vertices (also called search points) 314 and 316. In FIG. 3D we project the vertices 314 and 316 of the initial simplex to corresponding points 318 and 320 the Pareto front 322, while computing the SF score for each projected point. In FIG. 3E we then use a gradient-free search (i.e. simplex search) to search the Pareto front for a clinically acceptable treatment plan.

In one implementation, we perform projections by conducting a one-dimensional search using the bisection method [40] along a vector direction (see the segmented vector 324 in FIG. 3). In this one-dimensional search using the bisection method, we begin with a starting point and search along a vector direction for the feasibility boundary. At each iteration of this feasibility search, we compute the midpoint of the current interval (at the beginning this interval is defined by the start and end points) and evaluate whether the midpoint is a feasible plan. If the bisection method has not converged, we then select a new interval—either as the start point and midpoint or the midpoint and end point—and continue the feasibility search.

We define the coordinates of a point p in the decision variable space as $(c_1, c_2, \ldots, c_n)$ (i.e. 314 and 316 in FIG. 3D), the coordinates of a projected point p' on the Pareto front as $(c'_1, c'_2, \ldots, c'_n)$ (i.e. 318 and 320 in FIG. 3), and the SF score of the projected point as $f(p')$. We can then formulate the iterative treatment planning problem as a feasibility search using Equation 3.

$$\min_x \frac{1}{N_{ptv}} \sum_{j \in ptv} (d_i - D_p)^2 \quad (3)$$

s.t. $x \geq 0$ $\vec{d} = D\vec{x}$ $c_{EUD,rectum} \leq c_1$ $c_{EUD,bladder} \leq c_2$ $c_{EUD,FHR} \leq c_3$ $c_{EUD,FHL} \leq c_4$ $c_{EUD,body} \leq c_5$ $D_{ptv}(95\%) \geq D_p$ $D_{ptv}(\min) = 0.97 D_p$ $D_{ptv}(\max) = 1.1 D_p$ We note that POPS performs equally well if other constraints are chosen besides equivalent uniform dose (EUD) (i.e. mean, max, and DVH constraints). In this feasibility search, we minimize the placeholder objective of the squared difference in dose between PTV voxels and the prescription dose $D_p$. The values $c_1, \ldots, c_5$ can be conceptualized as bounds on the EUD constraints for various OARs.

For clarity and ease of visualization, the present description focuses on the example of a hypothetical 2D case. However, our POPS technique generalizes to n-dimensional cases, and results are provided in later sections for 5D prostate IMRT cases.

POPS Technique Implementation

Step 1. Define the Bounds $p_{b,1}, p_{b,2}, \ldots, p_{b,n}$ for the Decision Variable Search Space by Projecting a Seed Point $p_s$ onto the Pareto Front.

When projecting the seed point to define the decision space bounds, we perform the one-dimensional search by tightening the EUD constraint in one OAR (while fixing all other constraints) and repeat this projection for each OAR (five times total for a 5D prostate case). The projected points will form the bounds for the decision space and can be visualized as a simplex (see FIG. 3b).

As visualizations for n-D are too difficult, we instead provide visualizations in 2D where the feasibility search space is in $R^2$ while the decision space is the line bounded by the initial projected points. For a n-dimension treatment planning problem, the constraint feasibility search space is in $R^n$ while the decision space is a simplex bounded by n points that are found by projecting the seed point along orthogonal directions.

Step 2. Within the Bounded Decision Space, Define the Initial Simplex Vertices (Search Points) $p_1, p_2, \ldots, p_n$.

For simplicity, we define our initial vertices by taking the weighted average of the boundary points. In our subsequent description, we interchangeably use the terms "search points" and "simplex vertices" to describe points in the decision variable search space.

$$\tau_{i,j} = \begin{cases} 0.3, & \text{if } i = j \\ 1, & \text{otherwise} \end{cases} \quad (4)$$

$$p_i = \frac{\sum_{j=1}^{n} p_{b,j} \tau_{i,j}}{\sum_{j=1}^{n} \tau_{i,j}} \quad (5)$$

Here, $\tau_{i,j}$ refers to the weights assigned to each boundary point $p_{b,j}$. Prior knowledge can also be incorporated in the form of better starting simplex vertices, but our implementation uses a more straightforward initialization for reproducibility.

Step 3. Project Each of the Simplex Vertices $p_1, p_2, \ldots, p_n$ from the Decision Space to the Pareto Front to Obtain the Projected Points $p'_1, p'_2, \ldots, p'_n$, Again Using the Bisection Method.

Projection of the simplex vertices to the Pareto front is visualized for the 2D case in FIG. 3d. Similar to the projection of the seed point, all subsequent projections use the bisection method [40] to perform a one-dimensional search along a fixed vector direction. To determine this vector direction, we empirically chose to calculate the vector from the centroid of the initial simplex to the origin. Alternative choices to calculate the vector direction, such as choosing the normal vector to the decision variable plane, can work just as well. Example visualizations for one-dimensional search along this vector direction are shown as solid black lines in FIG. 3.

Step 4. Compute the Function Evaluation (i.e. SF Score) for Each of the Projected Simplex Vertices to Obtain $f(p_1')$, $f(p_2'), \ldots, f(p_n')$.

We can compute the SF score for a particular treatment plan solution p using Equations 1 and 2.

Step 5. Order the Simplex Points by their Function Evaluations Such that $f(p_1') \leq f(p_2') \leq \ldots \leq f(p_n')$ Steps 5-11 are adapted directly from the Nelder-Mead Simplex Search algorithm. Simplex search terminates when convergence criteria are met or the algorithm has reached the maximum number of iterations allowed. We define these termination criteria as (1) the maximum Euclidean distance between simplex vertices must be smaller than 5 Gy and (2) the maximum absolute difference between all plan SF scores must be smaller than 0.05.

Step 6. Compute the Centroid $p_c$ of the n−1 Best Simplex Points

Step 7. Reflection:
  a. Compute the reflected point in the decision space as $p_r = p_c + \alpha(p_c - p_n)$. We follow the official MATLAB version and use $\alpha = 1$.
  b. Project the reflected point to the Pareto front to obtain $p_r'$.
  c. Compute the function evaluation $f(p_r')$.
  d. If $f(p'_1) \leq f(p_r') < f(p'_{n-1})$, replace the worst simplex point with $p_r$ and start from 5.

Step 8. Expansion:
  a. If $f(p_r') < f(p'_1)$, compute the expansion point in the decision space as $p_e = p_c + \beta(p_c - p_n)$. We follow the official MATLAB version of the Nelder-Mead Simplex Search and use $\beta = 2$.
  b. Project the expansion point to the Pareto front to obtain $p'_e$.
  c. Compute the function evaluation $f(p_e')$.
  d. If $f(p_e') < f(p'_r)$, replace the worst simplex point with $p_e$ and start from 5.
  e. Otherwise, replace the worst simplex point with $p_r$ and start from 5.

Step 9. Outside Contraction:
  a. If $f(p'_{n-1}) \leq f(p_r') < f(p'_n)$, compute the outside contraction point in the decision space as $p_{oc} = p_c + \gamma(p_r - p_c)$. We follow the official MATLAB version and use $\gamma = 0.5$.
  b. Project the outside contraction point to the Pareto front to obtain $p_{oc}'$.
  c. Compute the function evaluation $f(p_{oc}')$.
  d. If $f(p_{oc}') < f(p'_r)$, replace the worst simplex point with $p_{oc}$ and start from 5.
  e. Otherwise, continue to step 11

Step 10. Inside Contraction:
  a. If $f(p'_n) \leq f(p_r')$, compute the inside contraction point in the decision space as $p_{ic} = p_c + \gamma(p_n - p_c)$. We follow the official MATLAB version and use $\gamma = 0.5$.
  b. Project the inside contraction point to the Pareto front to obtain $p_{ic}'$.
  c. Compute the function evaluation $f(p_{ic}')$.
  d. If $f(p_{ic}') < f(p'_n)$, replace the worst simplex point with $p_{ic}$ and start from 5.
  e. Otherwise, continue to step 11

Step 11. Shrink:
  a. Replace every point except the best point (i.e. $p_i$ where i=2, ..., n) with $p_i = p_1 + \rho(p_i - p_1)$. We follow the official MATLAB version and use $\rho = 0.5$.
  b. Start from step 5

Results

Experimental Setup and Evaluation

To determine the proficiency of our automated POPS technique, we compare POPS generated IMRT treatment plans to gold-standard VMAT treatment plans created as part of routine clinical workflow. While these human-created treatment plans are not necessarily Pareto optimal, they provide a benchmarking baseline in terms of clinical acceptability. Currently, treatment plan evaluation does not have a widely adopted evaluation metric for comparing treatment plans in regards to clinical acceptability. Instead, it is common to perform quantitative analysis of a plan's statistics.

To perform treatment plan evaluation, it is important to evaluate plans based on dose conformity, dose homogeneity, and OAR sparing [30], [42]-[48]. We adopt the following definition of the conformity index (CI) [48] and homogeneity index (HI) [47] to assess dose conformity and homogeneity, respectively:

$$CI = \frac{(TV_{95D_p})^2}{TV \times V_{95D_p}} \quad (6)$$

$$HI = \frac{D_5 - D_{95}}{D_p} \quad (7)$$

In order to assess OAR sparing, we compute the DVH values at five uniformly sampled control points (D(20%), D(40%), D(60%), D(80%), D(98%)). Lower dosage values at each of these control points implies better OAR sparing. We additionally conduct a Wilcoxon signed-rank test comparing plan statistics.

The dataset used in our experiment has 21 prostate cases acquired from the clinic following Stanford IRB protocol #41335. Scanner details, acquisition dates, and is treating physician varied across cases. Gold-standard VMAT treatment plans used two full coplanar arcs and were created by a human planner using a treatment planning system from Varian Medical Systems. Various OARs (including the rectum, bladder, left/right femoral heads, and body) were contoured, along with the PTV. In order to mitigate the effect of beam angle selection on plan quality and help control for dosimetric differences between IMRT and VMAT, we use a plan setting of 9 equally spaced photon beams (from 0° to 360° in increments of 40°). All POPS plans used a prescription dose of 74 Gy delivered over 40 fractions, a bixel size of 5 mm, and a dose voxel size of 3×3×3 mm³. Our POPS technique additionally implements the open-source MatRad software package to perform inverse planning [4] which uses a pencil-beam dose calculation algorithm and IPOPT [49].

Note that prior works have shown that prostate VMAT plans tend to have better dosimetric quality than IMRT plans [9]-[11]. However, we compare POPS results for IMRT to results for VMAT planning as we do not have access to a more relevant clinical IMRT dataset. VMAT planning, moreover, represents a current gold-standard in the clinic. POPS may be extended to VMAT planning.

Quantitative Comparison

Tables 2 and 3 provide further quantitative comparison between dosimetrist generated VMAT plans and POPS generated IMRT plans. To evaluate OAR sparing, five DVH control points (D(20%), D(40%), D(60%), D(80%), D(98%)) were selected to provide an approximation of the DVH curve for each OAR. Similarly, we evaluate dose conformity and homogeneity using the CI and HI, respectively. All differences were quantified using the Wilcoxon signed-rank test (p<0.05), and p-values were corrected using the Holm-Bonferroni method to control family-wise error rate [50].

Dose conformity values are summarized in Table 2, where CI approaches 1 for an ideal case. Plans produced using POPS and those produced by a human planner had comparable dose conformity. CI values for both POPS plans and gold-standard plans are within an acceptable range and comparable to values reported in previous work for prostate VMAT cases [44].

Dose homogeneity values are also provided in Table 2, where smaller HI values are better. Here, gold-standard VMAT plans provided more homogeneous dose distributions than those for POPS IMRT plans. Both POPS and the gold-standard plans had better HI values than reported in previous work [44], and both were within a clinically acceptable range.

TABLE 2

Comparison of CI and HI for POPS IMRT plans and gold-standard VMAT plans created manually. CI values approaching 1 are better, and smaller HI values are better.

|  | Conformity Index (CI) | Homogeneity Index (HI) |
|---|---|---|
| Manual VMAT | 0.862 (0.026) | 0.046 (0.010) |
| POPS IMRT | 0.831 (0.051) | 0.104 (0.001) |
| Wilcoxon signed-rank test p-value | 0.08503 | 0.00214 |

Similarly, dosage values are comparable between the two methods, demonstrating comparable OAR sparing. While POPS generally performs better for the rectum, femoral heads, and body, it performs slightly worse for the bladder, which may be due to a different emphasis on the bladder in manual plans. Modifying the emphasis on the bladder by changing its weighting in the scoring function could help to reduce this discrepancy and would be a possible avenue for future work. Of the 25 DVH control points evaluated here, POPS plans had significantly better OAR dosages for 13 control points, worse dosages for 2 control points, and similar dosages for 8 control points. Overall, POPS produces Pareto optimal plans that are highly comparable to dosimetrist generated plans with regards to clinical acceptability.

planning parameters and perform inverse planning until a clinically acceptable solution is found. However, an acceptable treatment plan that just satisfies clinical dosimetric criteria is not necessarily the most efficient, and perhaps plan parameters can be tuned further until a planner finds the best achievable plan. The decision-making process of treatment planners could be interpreted as optimizing treatment plans for both acceptability and efficiency. This process is often both time-consuming and labour intensive for planners. For IMRT cases, active planning time—planning time that directly utilizes a human planner's decisions or actions—has been reported to be on the order of 135 minutes, with active planning time potentially increasing for more complex cases [32].

Endeavouring to reduce active planning time, a variety of automated approaches have been proposed in literature, which we introduced in earlier sections. Of these various approaches, MCO methods attempt to produce Pareto optimal solutions. Where a posteriori MCO (database MCO) approaches attempt to generate the entire Pareto front (or at least approximate the Pareto front) [20], [31], [32], a priori MCO approaches select a Pareto optimal plan based on physician-defined preferences for objective weights and dose constraints[12], [33], [52], [53]. Both types of MCO approaches produce Pareto optimal plans but delegate the task of selecting clinically acceptable plans to the physician, either explicitly (i.e. in the case of a posteriori MCO) or implicitly through preferences (i.e. in the case of a priori MCO).

TABLE 3

Comparison of DVH values for five uniformly selected control points (D(20%), D(40%), D(60%), D(80%), D(98%)) between dosimetrist generated and POPS generated plans. Lower dosage values are better as they imply better OAR sparing. The significantly lower dosage values and significant p-values are bolded (significance when p < 0.05).

|  | OAR | D(20%) (Gy) | D(40%) (Gy) | D(60%) (Gy) | D(80%) (Gy) | D(98%) (Gy) |
|---|---|---|---|---|---|---|
| Manual VMAT | Rectum | 52.5 (10.9) | 32.0 (7.9) | 20.6 (7.1) | 9.7 (5.1) | 3.0 (1.1) |
|  | Bladder | 35.7 (21.2) | 14.8 (11.7) | 6.8 (7.0) | 3.8 (5.0) | 2.0 (2.6) |
|  | FH R | 24.2 (4.8) | 19.8 (4.3) | 14.8 (4.0) | 7.3 (4.3) | 2.2 (3.0) |
|  | FH L | 22.4 (4.6) | 17.4 (3.3) | 13.4 (3.2) | 6.9 (4.3) | 2.1 (2.9) |
|  | Body | 3.4 (1.7) | 0.6 (0.2) | 0.2 (0.1) | 0.1 (0.0) | 0* |
| POPS IMRT | Rectum | 48.7 (10.7) | 27.0 (8.7) | 13.7 (4.8) | 6.0 (2.5) | 2.3 (1.3) |
|  | Bladder | 46.5 (18.6) | 24.3 (15.9) | 10.9 (8.5) | 4.9 (4.9) | 2.1 (3.0) |
|  | FH R | 20.8 (4.3) | 15.0 (5.3) | 7.9 (4.3) | 4.3 (2.1) | 1.2 (1.0) |
|  | FH L | 20.3 (4.1) | 13.5 (4.6) | 7.2 (3.8) | 3.6 (1.3) | 1.1 (1.0) |
|  | Body | 3.2 (1.9) | 0.2 (0.5) | 0.1 (0.0) | 0* | 0* |
| Wilcoxon signed-rank test p-value | Rectum | 0.13653 | 0.09424 | 0.01174 | 0.00353 | 0.01274 |
|  | Bladder | 0.00214 | 0.00214 | 0.09064 | 0.87571 | 0.39163 |
|  | FH R | 0.06271 | 0.01823 | 0.00448 | 0.00618 | 0.02378 |
|  | FH L | 0.18262 | 0.01274 | 0.00214 | 0.00214 | 0.01866 |
|  | Body | 0.39163 | 0.01328 | 0.01328 |  |  |

*Values were vanishingly small

Discussion

This study introduced a fully automated treatment planning algorithm, POPS. POPS combines projections using the bisection method and a gradient-free search to produce treatment plans that are both Pareto optimal and clinically acceptable. To evaluate clinical acceptability, we compare performance for POPS IMRT planning to performance for VMAT planning by dosimetrists, the current gold-standard.

POPS Vs Other Approaches

Automated treatment planning approaches have steadily grown in popularity due to their potential to drastically reduce active planning time [13], [14], [23], [27], [28], [30], [32], [51], [52]. Following the iterative approach to treatment planning, human planners repeatedly adjust treatment While we do not have access to the implementations of other MCO algorithms in the MatRad framework, we report their active planning times for rough comparison in Table 4. Our initial implementation of POPS requires no active planning from human planners. To the best of our knowledge, POPS is currently the only approach capable of producing Pareto optimal and clinically acceptable plans with no active planning required. Alternative a posteriori MCO approaches, for reference, require a human planner to select clinically acceptable plans from a database of Pareto optimal solutions, resulting in longer active planning times compared those for POPS.

TABLE 4

Comparison of average computation times and active planning times required for each patient. As compared to traditional MCO approaches, POPS trades active planning time for background computation time, allowing dosimetrists and physicians to better allocate their time in the clinic. For this study, we define active planning time as planning time that directly utilizes a human planner's decisions or actions.

| Method | Active Planning Time/Patient | Computation Time/Patient | Total Time/Patient |
|---|---|---|---|
| Human Planner* | 135 min | N/A | 135 min |
| Approximated MCO (with RayStation implementation)* | 12 min | 7 min | 19 min |
| POPS (with MatRad implementation) | 0 min | 78 min | 78 min |

*Based on reported average time from Craft et al. [32]

One major benefit of having no active planning time is that many patients can be run in parallel, reducing the average time overall per patient and allowing for great scalability to servers or clusters. For our 5D prostate IMRT implementation, POPS utilizes 5 CPU threads. On our consumer-level desktop Ryzen 2700x CPU (16 threads), up to 3 patients may be run simultaneously, which scales to potentially 25 patients on a Ryzen 3990x workstation and even more when factoring in servers or a gpu-based implementation. Similarly, having no active planning requirement allows physicians and dosimetrists to better allocate their time in the clinic, potentially spending it on more demanding and relevant tasks.

Overall, the POPS technique directly searches the Pareto front for clinically acceptable treatment plans, as defined by a scoring function. We note that the particular scoring function can be interchanged, as desired, without affecting the functionality of the POPS technique. In contrast to previous categories of MCO approaches, POPS automates the selection process of a clinically acceptable plan. In practice, POPS provides a general framework that allows for the direct search of the Pareto front. Based on results for 21 prostate cases, POPS IMRT plans have comparable dose conformity and OAR sparing with slightly worse dose homogeneity, as compared to VMAT plans produced in clinical workflow.

The scoring function used by POPS incorporates clinical acceptability criteria (Table 1) proposed in previous work [38]. As treatment plan evaluation can be subjective, we certainly acknowledge that physicians can choose criteria that may be somewhat different from what we adopted in the present study. To that end, Table 1 can be modified as desired to better suit individual preferences without affecting the performance of the POPS technique. Similarly, we found our heuristics to work well for prostate IMRT planning, but they may also be modified, resulting in different hyperparameter values, to suit different anatomies or physician preferences. The POPS framework allows for the implementation of alternative scoring functions or clinical acceptability criteria. For a given scoring function and set of criteria, POPS produces treatment plans that satisfy the overall objective of this study: to produce treatment plans that are both Pareto optimal and clinically acceptable in a fully automated fashion.

Potential Improvements to Speed

Based on the reported computation times from Craft et al., MCO approaches that utilize approximations of the Pareto front typically have computation times less than 10 minutes. Our current implementation, which uses the MatRad software package to is perform inverse planning and does not yet utilize Pareto front approximations, has computation times around an hour. As our computation times were measured using an implementation in MatRad, they may not be perfectly representative of commercial implementations, which leverage various approximations to improve computational efficiency. We would like to clarify that the computation time differences are not the result of POPS. Rather, they can be attributed to two main factors: inverse planning software implementation differences and the PGEN approximation method (or equivalent Pareto front approximation method). Each time POPS makes an adjustment to the search variables, the vast majority of time is spent in computing function evaluations (i.e. performing inverse planning), so the bottleneck to sequential throughput is inverse planning speed. We have implemented our POPS technique using the open source MatRad package so that our findings can be more easily verified by other studies, but implementation of POPS in alternative treatment planning software packages like Eclipse or RayStation or ConRad [3] will speed up computation accordingly.

For our implementation, we make no additional assumptions or approximations in regards to dose constraints or objectives (beyond those made by the matRad software package), but recent works such as ConRad demonstrate dramatic improvements to inverse planning throughput if certain approximations are made [3]. Similarly, as reported by Craft et al. [31], [32], their implementation uses the PGEN approximation of the Pareto front, requiring significantly fewer function evaluations to approximate the Pareto front. We hope to apply both improvements to our POPS technique in the future and anticipate similarly large increases in speed as were observed in their works.

Conclusion

External beam radiation therapy is used for treatment of a significant number of cancer patients[54]. Within the radiation therapy workflow, the treatment planning process represents a bottleneck to high quality patient care, due to the time-consuming nature of the iterative planning process and inter-planner variability. Previous works in automated planning can be generally categorized as KBP, PBP, and MCO approaches, each having key limitations. The POPS technique attempts to address these limitations and provides a fully automated framework for performing Pareto optimal treatment planning.

Evaluation of treatment plan quality is an especially subjective and nuanced process. While we acknowledge that particular scoring of treatment plans may differ according to planner expertise and preferences, we adopt a scoring function (SF) for the purpose of optimizing prostate treatment plan quality in regards to clinical acceptability criteria previously proposed in literature [38]. Through qualitative and quantitative analyses comparing IMRT plans produced by POPS with gold-standard VMAT plans produced as part of clinical workflow, we demonstrate that the POPS technique produces plans that are both Pareto optimal and clinically acceptable. While our initial implementation of POPS has longer computation times than alternative approaches, POPS is currently the only MCO-like approach that has no active planning time requirement. Overall, our results indicate that POPS can substantially improve treatment planning workflow.

Fully Automated Noncoplanar Radiation Therapy Treatment Planning

Here we present an important application of POPS to noncoplanar radiation therapy treatment planning. External beam radiation therapy (EBRT) involves the delivery of ionizing radiation to treat diseased tissue while sparing nearby organs-at-risk (OARs) (Galvin et al 2004, Timmerman and Xing 2012). In the case of intensity-modulated radiation therapy (IMRT), planners determine the appropriate plan configuration (i.e. radiation modality, incident beam directions, isocenter location, etc.) and perform inverse planning of individual beam fluences to satisfy various objectives and constraints (Fu et al 2019, Wieser et al 2017). Volumetric modulated arc therapy (VMAT), which allows for continuous rotational delivery of intensity-modulated fields (Otto 2008, Yu 1995, Unkelbach et al 2015, Crooks et al 2003), uses many of these same principles and has been shown to improve delivery efficiency while maintaining or improving dosimetric quality (Rao et al 2010, Verbakel et al 2009, Wolff et al 2009, QUAN et al 2012, Rosenthal et al 2010, Hardcastle et al 2011).

Clinical IMRT and VMAT have traditionally used equispaced coplanar angles and trajectories, where plans are created manually by experienced planners. Traditional techniques assume that incident beam directions are equispaced and coplanar, though plan quality can potentially be improved by adopting more intelligent angle sampling schemes and noncoplanar directions (Li and Xing 2011, 2013, Smyth et al 2019). Similarly, manual treatment planning can be time-consuming and labor intensive, and developing automated methods can substantially improve clinical workflow (Hussein et al 2018, Huang et al 2021). To address the limitations traditional techniques, we provide a technique called station parameter optimized radiation therapy (SPORT). Within the SPORT technique, various algorithms have been developed to address the limitations of equispaced IMRT and VMAT (i.e. segmentally boosted VMAT, DASSIM, etc.) (Li and Xing 2011, 2013, Xing and Li 2014). Here, we provide an application of the noncoplanar Pareto optimal projection search (NC-POPS) algorithm for fully automated noncoplanar treatment planning.

1.1 Beam Angle Optimization

Beam angle optimization (BAO), critically important to noncoplanar treatment planning, has traditionally not been a part of the coplanar treatment planning process. However, previous studies on noncoplanar IMRT and VMAT have revealed the potential for significant dosimetric improvements when comparing noncoplanar plans to their coplanar counterparts. In this part, we provide a brief overview of BAO approaches and direct interested readers to a more in-depth review for further reading (Smyth et al 2019).

BAO approaches are typically categorized into two different classes. The first class of approaches does not incorporate fluence map optimization (FMO) into the beam angle selection (BAS) process. Instead, these approaches typically select beam angles using heuristics based on geometric or dosimetric information (Bangert and Oelfke 2010, Smyth et al 2013, MacDonald and Thomas 2015, Yang et al 2011, Fix et al 2018). In contrast, the second class of approaches does incorporate FMO into the BAS process. For this class of methods, the BAS problem is typically formulated as a combinatorial optimization (CO) problem, where an ensemble of promising beam angles is selected from the feasible set of candidate beam angles (i.e. beam angles where there are no couch-gantry collisions). A comparison of several strategies for solving the CO problem was done previously by Bangert et al. (Bangert et al 2013), with many alternative strategies being proposed as well (Bangert et al 2013, Stein et al 1997, Pugachev et al 2001, Papp et al 2015, Hou et al 2003, Wu et al 2000, Li et al 2004, Wang et al 2003, Li et al 2005, Woudstra and Storchi 2000, Pugachev and Xing 2002).

1.2 Pareto Optimal Projection Search

The workflow for treatment planning traditionally has been a manual, iterative process performed by human planners. This iterative planning process is not only time-consuming and labor intensive, but the resulting plan quality varies with planner skill and experience (Clark et al 2008, Shen et al 2020, Roach et al 2019, Nelms et al 2012, Berry et al 2016, Batumalai et al 2013, Moore et al 2012, Xing et al 1999). For instance, in the case of prostate treatment planning, our clinical protocol usually places high priority on sparing organs like the rectum and bladder, with less priority placed on sparing organs like the femoral heads. However, individual planner preferences may vary, which can lead to substantial variations in plan quality. Addressing these issues by reducing active treatment planning time and inter-planner variability has tremendous potential for improving clinical workflow and quality of care.

The POPS technique was described above as applied to the coplanar setting. In this application, we provide substantial extensions of the algorithm to apply it to the noncoplanar setting by adapting an iterative approach (Bangert et al 2013, Papp et al 2015) to the CO problem.

2. Methods

Here, we propose the noncoplanar Pareto optimal projection search (NC-POPS) algorithm, which has two main steps: 1) BAO and 2) fully automated inverse planning using POPS. In this work, we focus on applying the present method to the noncoplanar IMRT setting. The present method, however, can also be applied to the noncoplanar VMAT setting (Papp et al 2015).

First, BAO is performed by solving the CO problem using an iterative approach with limited number of FMO iterations (Papp et al 2015). This iterative approach produces an ensemble of promising beam directions, which we call beam control points, to be used for noncoplanar IMRT planning. For noncoplanar VMAT, these beam control points are then converted to dynamic trajectories by solving a shortest path problem between beam control points, as described by Papp et al. (Papp et al 2015).

Second, given the set of beam control points or dynamic trajectories, fully automated inverse planning can be performed by applying the POPS technique. POPS searches the feasibility boundary, which contains the Pareto front, for the most desirable plans as determined by a given scoring function. In this work, we use a normalized equivalent uniform dose (nEUD), which normalizes the EUD of each OAR by the maximum dose.

2.1 BAO Using an Iterative Approach

Figure 4:
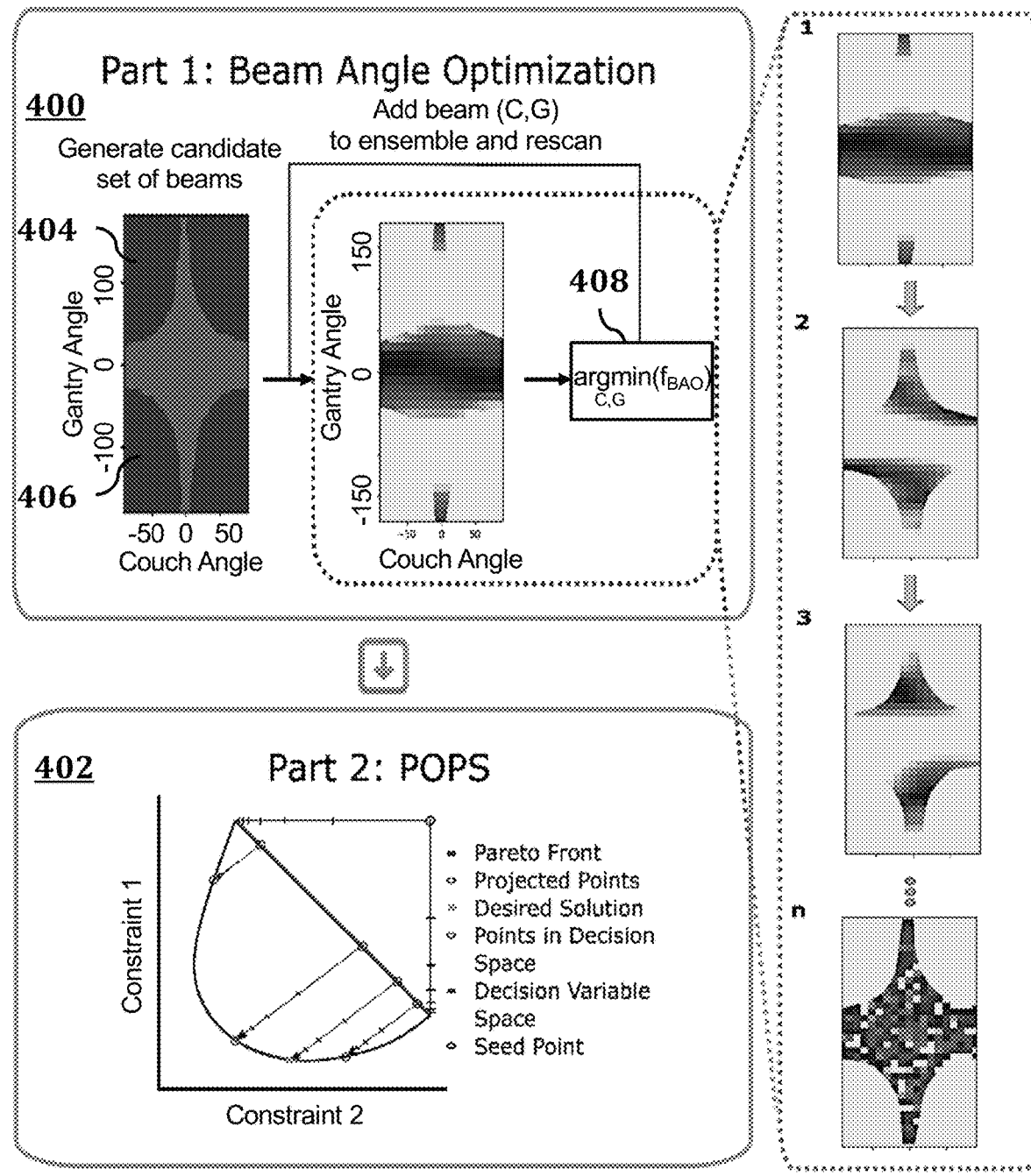
FIG. 4 visualizes the overall workflow for an application of an embodiment of the invention to beam angle optimization.

FIG. 4 visualizes the overall workflow for the NC-POPS method, which includes a first part 400 that performs BAO followed by a second part 402 that performs POPS. The BAO process 400 can be formulated as a combinatorial optimization problem where BAO is performed using an iterative approach. At each iteration $\eta$, we exhaustively search for the beam angle which minimizes $F_{BAO}$ and add it to the beam ensemble. Upon completion of BAO 400, we have an ensemble of n promising beam angles that can then be used to perform automated inverse planning using the POPS technique 402.

In this formulation, we attempt to create an ensemble of promising beam directions by iteratively adding beam angles (i.e. couch and gantry angle pairs) from the candidate set of feasible beams. We begin by determining which couch and gantry angle pairs are feasible and which lead to undesirable collisions. Beam angles that lead to collisions are excluded (e.g., regions 404 and 406 of FIG. 4). Next, an iterative approach is adopted to select promising beam angles (Bangert et al 2013, Papp et al 2015). In each iteration η of the approach, we perform fluence map optimization (FMO) for all feasible beam angles and add the best performing beam angle to the ensemble. The FMO problem during BAO follows the setup shown in Equations 1, 2, and 3, which differs from the setup used for automated inverse planning (Equations 4, 5, and 6).

$$EUD_s = \left(\frac{1}{N_s}\sum_{i \in s} d_i^{a_s}\right)^{1/a_s} \quad (1)$$

$$F_{BAO} = EUD_{ptv} + \sum_{s \in OARs} p_s EUD_s \quad (2)$$

$$\min_x F_{BAO}$$

$$\text{s.t. } x \geq 0$$

$$\vec{d} = D\vec{x} \quad (3)$$

In the BAO component of NC-POPS, we use the objective function $F_{BAO}$, which contains equivalent uniform dose objectives for the target and various OARs. Definitions for EUD and $F_{BAO}$ are shown in Equations 1 and 2. $p_i$ and $d_i$ refer to the penalty and dose, respectively, at voxel i in a particular structure s. $N_s$ refers to the total number of voxels in the structure s, and $a_s$ is a structure-specific EUD parameter. Other popular choices for this objective function include quadratic objective terms for the target, OARs, and distance-based dose conformity.

In the first iteration (η=1) of the approach, we perform an exhaustive search by running FMO for all feasible beam angles. The beam angle that provides the minimum objective function value is then added to the ensemble (denoted as $BE_\eta$). In the next iteration η+1, we compute the objective function values for combinations of each beam in the feasible set with the existing ensemble $BE_\eta$. We again search for the beam angle with the minimum objective function value and add it to the ensemble $BE_{\eta+1}$. This iterative approach, similar to previous implementations (Bangert et al 2013, Papp et al 2015), is repeated until the beam ensemble contains the desired number of beams.

Part 1 of FIG. 4 illustrates the iterative approach for BAO. Each iteration of the approach involves computing objective function values for the candidate beam angle combinations and adding the minimum beam angle combination 608 to the beam ensemble. In Table 5, we list the parameters relevant to the BAO process. To be consistent with our clinical protocol, higher emphasis (larger $p_s$ values) is placed on sparing the rectum and bladder, and less emphasis is placed on sparing the femoral heads. Additionally, higher emphasis is placed on the body objective (EUD with α=5), which acts as an indirect objective for dose conformity.

TABLE 5

List of parameters used in the beam angle optimization process.

|  | PTV | Rectum | Bladder | FH R | FH L | Body |
|---|---|---|---|---|---|---|
| Penalty (p_s) | 1 | 0.2 | 0.2 | 0.03 | 0.03 | 1 |
| Overlap Priority | 1 | 2 | 2 | 3 | 3 | 3 |
| EUD a | −20 | 1 | 1 | 1 | 1 | 5 |
| Ref. Dose (Gy) | 74 | 0 | 0 | 0 | 0 | 0 |

2.2 POPS for Fully Automated Inverse Planning

The POPS technique provides a general framework for fully automated inverse planning. Its main purposes are to produce plans that are Pareto optimal and clinically acceptable, while requiring no active planning time during the inverse planning process. The algorithm is visualized for a hypothetical 2D case in part 2 of FIG. 4, and the feasibility search setup is described in Equations 4, 5, and 6.

$$nEUD_s = \frac{EUD_s}{D_{max}} \quad (4)$$

$$F_{POPS} = \begin{cases} 1, & \text{if infeasible} \\ \dfrac{\sum_{s \in S} w_s \cdot nEUD_s}{\sum_{s \in S} w_s}, & \text{otherwise} \end{cases} \quad (5)$$

$$\min_x \frac{1}{N_{ptv}} \sum_{i \in ptv} (d_i - D_p)^2 \quad (6)$$

$$\text{s.t. } x \geq 0$$
$$\vec{d} = D\vec{x}$$
$$EUD_{rectum} \leq c_1$$
$$EUD_{bladder} \leq c_2$$
$$EUD_{FHR} \leq c_3$$
$$EUD_{FHL} \leq c_4$$
$$EUD_{body} \leq c_5$$
$$D_{ptv}(95\%) \geq D_p$$
$$D_{ptv}(\min) = 0.975 D_p$$
$$D_{ptv}(\max) = 1.05 D_p$$

TABLE 6

List of parameters used during POPS automated inverse planning. Prescription dose D_p = 74 Gy. Plan scoring (F_POPS) is performed using Equations 4 and 5, and the feasibility search is formulated in Equation 6.

|  | PTV | Rectum | Bladder | FH R | FH L | Body |
|---|---|---|---|---|---|---|
| Score Weight (w_s) | N/A | 1 | 1 | 0.15 | 0.15 | 5 |
| Overlap Priority | 1 | 2 | 2 | 3 | 3 | 3 |
| EUD a | N/A | 1 | 1 | 1 | 1 | 5 |

The main purpose of the POPS technique is to perform fully automated inverse planning. In radiation therapy, inverse planning can be conceptualized as a multicriteria optimization problem with many conflicting objectives and constraints.

Here, we formulate the inverse planning problem as a feasibility search with the various constraints shown in Equation 6. Thus, the overall goal of the POPS technique is to determine values of these various constraints (i.e. $c_1$ through $c_5$) that lead to Pareto optimal and clinically acceptable treatment plans. The POPS technique determines these constraint values by searching the feasibility boundary (which contains the Pareto front) for the most desirable plans, as defined by a scoring function.

In this application of POPS, we use a normalized equivalent uniform dose (nEUD) metric to score plans for the POPS technique, as shown in Equations 4 and 5. Here, $EUD_s$ refers to the equivalent uniform dose of the structure s, $D_{max}$ refers to the maximum dose ($1.05D_p$, where $D_p$ refers to the prescription dose), and $F_{POPS}$ is the scoring function used by the POPS technique to search the feasibility boundary. The POPS technique utilizes two main components to search the feasibility boundary: gradient-free search (e.g., Nelder-Mead simplex search)(Nelder and Mead 1965) and a projection (e.g., using the bisection method). For all plans generated using POPS, we use a prescription dose $D_p$ of 74 Gy. Table 6 lists the relevant parameters used during the POPS technique.

Results 3.1 Experimental Setup and Evaluation

We study the performance of our approach on a dataset of 21 prostate cases (Stanford IRB protocol #41335). Two baseline methods are included for comparison. For the first baseline method, clinical VMAT plans with two full coplanar arcs were manually planned by experienced planners using the Eclipse treatment planning software from Varian Medical Systems. For the second baseline method, 9-beam coplanar IMRT plans were generated automatically using the POPS technique. These baseline methods are compared against plans using NC-POPS, configured for 9-beam noncoplanar IMRT. For this current study, all treatment plans created using POPS utilize the open-source treatment planning software package called MatRad (Wieser et al 2017) and all dose distribution comparisons are done in MatRad. Additionally, these plans were generated for a 6 MV linear accelerator, utilizing a dose grid size of 3×3×3 mm and a bixel width of 5 mm.

Treatment plans were evaluated based on dose conformity, dose homogeneity, and OAR sparing (Yang et al 2020, Pyakuryal et al2010, Ventura et al2016, Cao et al2019, Kataria et al 2012, van't Riet et al 1997, Semenenko et al 2008, Paddick 2000). We adopt the following definitions (Equations 7 and 8) of the conformity index (CI) (Paddick 2000) and homogeneity index (HI) (Semenenko et al 2008):

$$CI = \frac{(TV_{95D_p})^2}{TV \times V_{95D_p}} \quad (7)$$

$$HI = \frac{D_5 - D_{95}}{D_p} \quad (8)$$

In order to assess OAR sparing, we compute the mean dose and dose-volume histogram (DVH) values at the following percentiles: D(20%), D(40%), D(60%), D(80%), and D(98%). Here, lower dosage values are desirable as they imply better OAR sparing.

3.2 Qualitative Comparison

Figure 5:
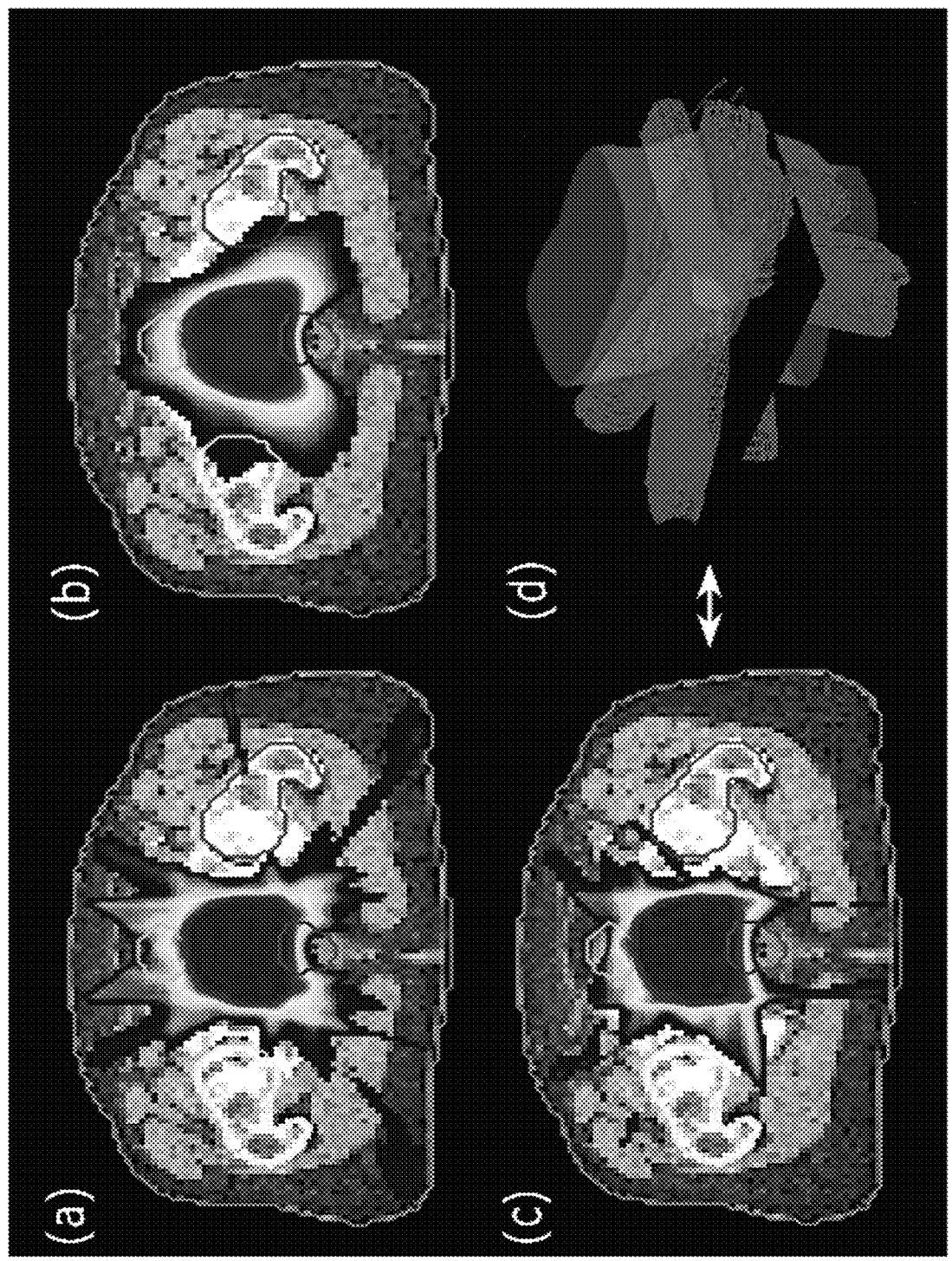
FIG. 5 shows example dose distributions for the POPS coplanar IMRT plan, Manual coplanar VMAT plan, and NC-POPS IMRT plan, as well as a visualization of the 3D rendered noncoplanar beam directions.

We first conduct a qualitative comparison between the two types of coplanar baseline plans and the NC-POPS plans. FIG. 5 shows example dose distributions for the (a) POPS coplanar IMRT plan, (b) Manual coplanar VMAT plan, and (c) NC-POPS IMRT plan. Part (d) provides a visualization of the 3D rendered noncoplanar beam directions.

Comparing the dose distribution for the NC-POPS method to either of the coplanar baselines, we can visually appreciate a substantial improvement in OAR sparing with comparable conformity and homogeneity. In FIG. 5 (d), we visualize a rendering of the beam ensemble created using BAO. The ensemble of promising beam angles is highly noncoplanar, with fewer OAR voxels in the paths of the selected beams than in the coplanar setting.

Figure 6A:
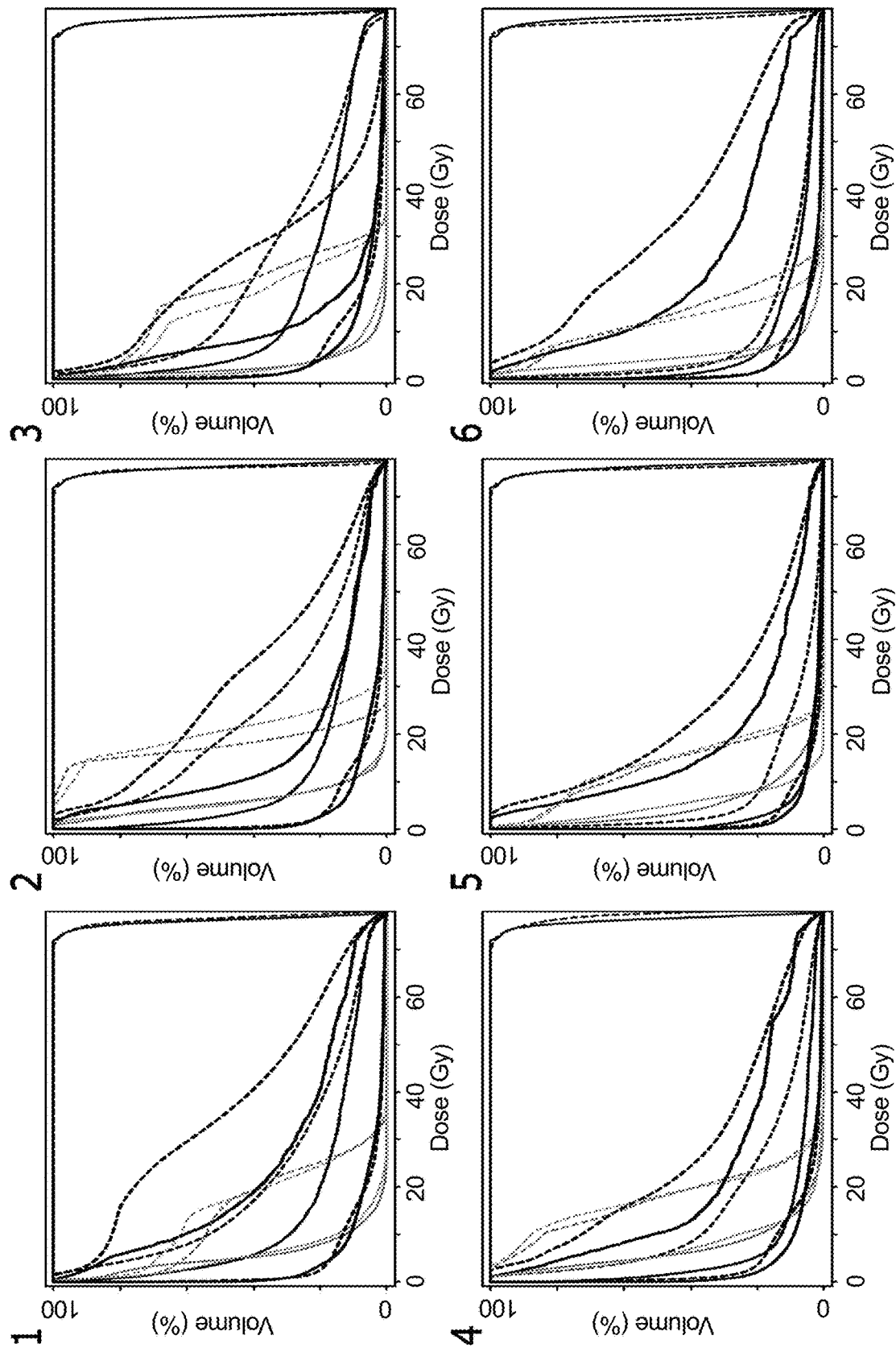
FIG. 6A and FIG. 6B provide DVH comparisons between an embodiment of the invention applied to beam angle optimization and the coplanar baselines for six example patients.
Figure 6B:
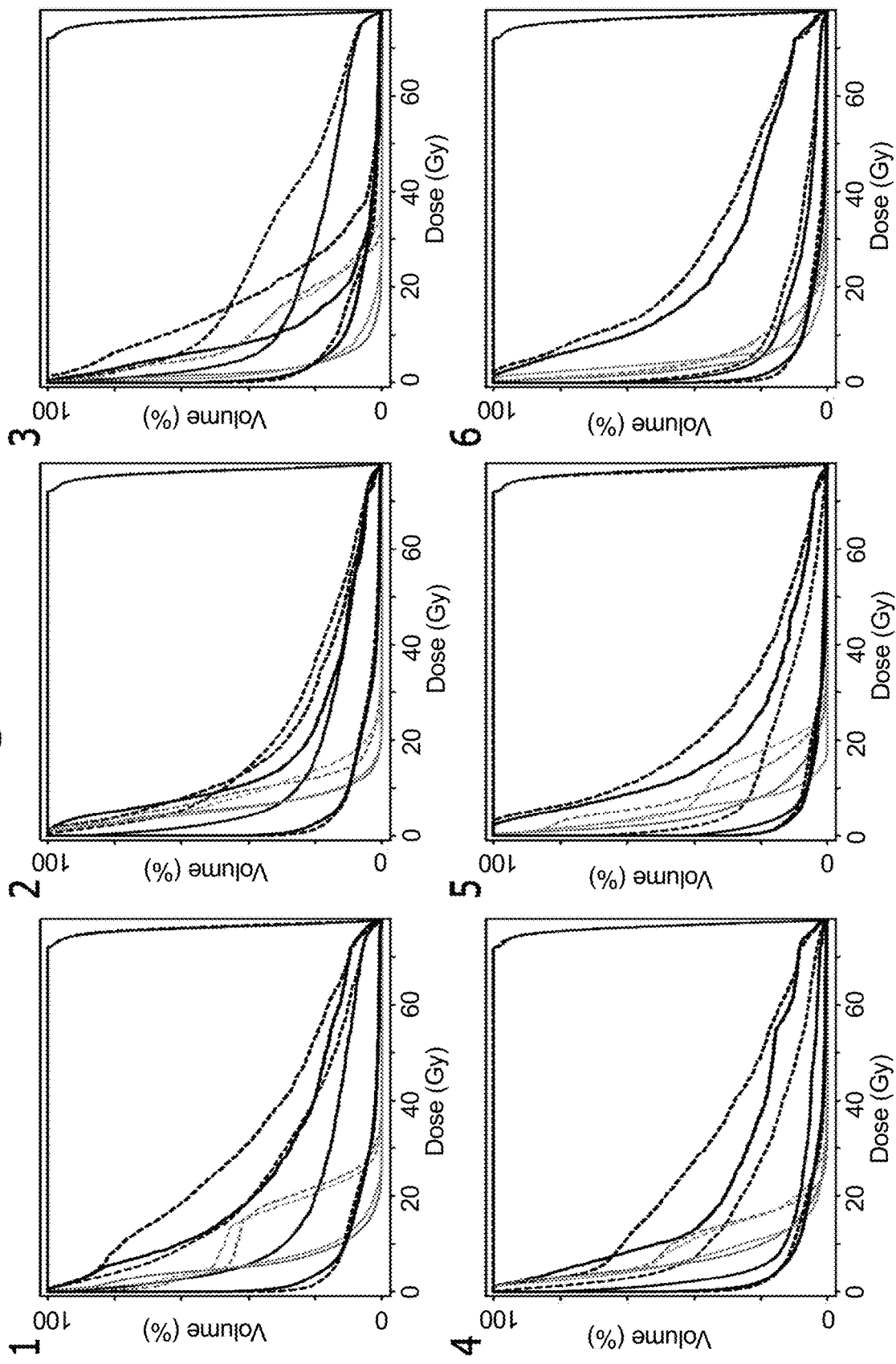

FIG. 6A and FIG. 6B provide DVH comparisons between NC-POPS and the coplanar baselines (see FIG. 6A and FIG. 6B for six example patients (numbered 1-6). In FIG. 6A, we compare the performance of NC-POPS IMRT plans (solid lines) to that of the manual coplanar VMAT plans (dashed lines). In each of the six patients, OAR sparing for all organs is significantly improved by the present method. In FIG. 6B, we compare the performance of NC-POPS IMRT plans (solid lines) to the performance of coplanar POPS IMRT plans (dashed lines) for the same six patients shown in FIG. 6A. OAR sparing of the NC-POPS method is significantly better for all structures except the body. PTV performance was comparable between NC-POPS and the coplanar baselines for all example patients. The NC-POPS IMRT plans provide substantially better OAR sparing than either the manual coplanar VMAT plans or the coplanar POPS IMRT plans.

3.3 Quantitative Comparison

In Table 7, the NC-POPS method is compared to the two coplanar baseline methods. Plan quality is assessed using the conformity index, the homogeneity index, and various OAR sparing statistics (mean dose, D(20%), D(40%), D(60%), D(80%), and D(98%)). Here values like D(•%) represent metrics for the DVH and can be interpreted as (•%) of the structure receives at least D (•%) dose. Differences between the evaluated methods were quantified using the Wilcoxon signed-rank test ($p<0.05$).

Dose conformity values are summarized in Table 7, with CI values approaching 1 in an ideal case. The NC-POPS method achieves significantly better conformity than the manual coplanar baseline and comparable conformity to the POPS coplanar baseline (p-values of 0.00313 and 0.83479, respectively). Dose homogeneity values were additionally compared in Table 7, where HI approaches zero for an ideal case. Dose homogeneity values for the evaluated methods were comparable.

Finally, OAR sparing is assessed using the mean dose and various DVH metrics. The is NC-POPS method achieves the best OAR sparing among the evaluated methods with significantly lower mean doses to the rectum, bladder, and femoral heads than either of the two coplanar baseline methods. Moreover, the present method achieves the lowest values in most of the OAR DVH metrics that were evaluated. Overall, the NC-POPS method achieves better OAR sparing, comparable or better dose conformity, and comparable dose homogeneity when compared to the two coplanar baseline methods.

TABLE 7

DVH values at five percentiles (D(20%), D(40%), D(60%), D(80%), D(98%)) were used to compare OAR sparing.
Conformity and homogeneity are additionally assessed. The best values are bolded for readability.

|  | Conformity Index (CI) | Homogeneity Index (HI) | OAR | Mean Dose (μ) | D(20%) (Gy) | D(40%) (Gy) | D(60%) (Gy) | D(80%) (Gy) | D(98%) (Gy) |
|---|---|---|---|---|---|---|---|---|---|
| Manual Coplanar VMAT | 0.86 (0.03) | 0.05 (0.01) | Rectum | 30.2 (5.6) | 51.2 (10.6) | 31.2 (7.6) | 20.0 (6.9) | 9.4 (5.0) | 3.0 (1.0) |
|  |  |  | Bladder | 19.2 (9.5) | 34.8 (20.7) | 14.5 (11.4) | 6.6 (6.8) | 3.7 (4.9) | 1.9 (2.5) |
|  |  |  | FH R | 16.4 (3.4) | 23.6 (4.7) | 19.3 (4.2) | 14.4 (4.0) | 7.1 (4.2) | 2.2 (2.9) |
|  |  |  | FH L | 15.0 (3.1) | 21.9 (4.6) | 17.0 (3.3) | 13.0 (3.2) | 6.8 (4.2) | 2.1 (2.8) |
|  |  |  | Body | 3.9 (0.8) | 3.3 (1.6) | 0.5 (0.2) | 0.2 (0.1) | 0.1 (0.0) | 0* |
| Coplanar POPS 9-Beam IMRT | 0.90 (0.03) | 0.05 (0.00) | Rectum | 26.0 (6.3) | 46.2 (11.7) | 25.7 (8.7) | 14.0 (5.9) | 6.4 (3.9) | 2.4 (1.9) |
|  |  |  | Bladder | 19.0 (8.8) | 36.5 (20.0) | 13.7 (11.8) | 5.8 (6.6) | 3.0 (4.3) | 1.3 (2.4) |
|  |  |  | FH R | 8.6 (2.2) | 15.6 (3.9) | 8.7 (3.7) | 4.2 (2.1) | 2.1 (1.0) | 0.6 (0.5) |
|  |  |  | FH L | 8.6 (2.3) | 16.1 (4.2) | 8.2 (3.9) | 3.8 (1.5) | 1.9 (0.9) | 0.5 (0.5) |
|  |  |  | Body | 3.7 (0.8) | 2.4 (1.6) | 0.2 (0.3) | 0.1 (0.0) | 0* | 0* |
| NC-POPS 9-Beam IMRT | 0.90 (0.04) | 0.05 (0.00) | Rectum | 21.9 (6.3) | 38.1 (14.8) | 18.1 (7.6) | 10.1 (3.6) | 5.7 (2.0) | 2.2 (1.2) |
|  |  |  | Bladder | 14.3 (8.7) | 25.1 (22.2) | 8.5 (9.4) | 3.5 (4.1) | 1.7 (2.3) | 0.6 (1.3) |
|  |  |  | FH R | 5.7 (1.5) | 9.1 (2.9) | 5.1 (1.6) | 3.0 (1.2) | 1.7 (0.8) | 0.7 (0.4) |
|  |  |  | FH L | 5.7 (1.4) | 8.8 (2.5) | 5.5 (1.6) | 3.3 (1.2) | 1.9 (1.0) | 0.8 (0.6) |
|  |  |  | Body | 3.7 (0.8) | 3.3 (1.6) | 0.4 (0.4) | 0.1 (0.0) | 0* | 0* |

|  |  | Conformity Index (CI) | Homogeneity Index (HI) | Rectum (μ) | Bladder (μ) | FH R (μ) | FH L (μ) | Body (μ) |
|---|---|---|---|---|---|---|---|---|
| NC-POPS vs. Manual Coplanar VMAT | Wilcoxon Signed-rank Test (p-value) | 0.00313 | 0.12717 | 0.00006 | 0.00014 | 0.00006 | 0.00006 | 0.01295 |
| NC-POPS vs. Coplanar POPS | Wilcoxon Signed-rank Test (p-value) | 0.83479 | 0.54617 | 0.00006 | 0.00028 | 0.00006 | 0.00006 | 0.35701 |

*Values were vanishingly small

4. Discussion

We have presented the NC-POPS method for fully automated noncoplanar treatment planning. NC-POPS provides substantial extensions of the POPS technique to the noncoplanar setting by incorporating BAO using an iterative algorithm. The performance of the NC-POPS method for IMRT was compared to two coplanar baseline methods (coplanar POPS IMRT and manual coplanar VMAT). Here, we evaluated the performance of our method on a dataset of prostate cases, but we anticipate that the method can be readily applied to the treatment planning of other sites in the body, with slight modifications to Equations 3 and 6.

Here, we implemented an iterative approach to BAO, though many alternative approaches to the BAO problem also exist (e.g. simulated annealing, genetic algorithms, cross-entropy algorithms, etc.). While comprehensive comparisons of various BAO approaches are scarce, previous works like Bangert et al. (Bangert et al 2013) conclude that the performance of various BAO approaches is similar. Bangert et al. argues that this comparable performance is likely due to convergence of these various methods to solutions that have similar BAO objective function values. In the implementation described here, we adopt the iterative approach to BAO, or "lookahead strategy," developed previously due to its simplicity and improved computational efficiency (Bangert et al 2013, Papp et al 2015).

To perform fully automated treatment planning, the NC-POPS method incorporates the POPS technique to search the feasibility boundary, which contains the Pareto front, for the most desirable plans. Plan scoring is performed using the nEUD metric, where high priority is placed on sparing organs like the rectum and bladder, and low priority is placed on sparing organs like the femoral heads. These specific organ priorities are adopted to mimic our clinical protocol.

The NC-POPS method achieves significantly better OAR sparing, significantly better dose conformity than the manual coplanar baseline, and comparable homogeneities to both coplanar baseline methods. Moreover, the two main components of NC-POPS, namely BAO and POPS, are both modular and can be incorporated into existing clinical workflows. The framework can also be readily upgraded to incorporate new developments to either BAO or automated treatment planning.

The current framework may also be applied to the noncoplanar VMAT setting, as well as to treatment planning of other sites in the body (i.e. head and neck, abdomen, etc.). The BAO component of our framework has previously been applied (Bangert et al. 2013, Papp et al. 2015) to manual noncoplanar IMRT and manual noncoplanar VMAT. In the case of noncoplanar VMAT, the ensemble of promising beam directions produced by BAO can be converted to a dynamic trajectory by solving a traveling salesman problem (Papp et al 2015). Similarly, applying POPS to automated VMAT treatment planning can be done by applying additional steps after FMO, such as leaf sequencing and direct aperture optimization (Otto 2008, Christiansen et al 2018, Papp and Unkelbach 2014).

5. Conclusion

We have described the NC-POPS framework for fully automated noncoplanar treatment planning. The first component of the framework, BAO, is implemented using an iterative algorithm to produce an ensemble of promising noncoplanar beam directions. These beam directions are then used in the second component of the framework, POPS, to perform fully automated inverse planning. Our experimental results demonstrate that the NC-POPS significantly improves OAR sparing as compared to coplanar methods, while maintaining comparable or better dose conformity and comparable homogeneity. We anticipate that the present method will substantially improve clinical workflow and plan quality.

REFERENCES

[1] J. M. Galvin et al., "Implementing IMRT in clinical practice: a joint document of the American Society for Therapeutic Radiology and Oncology and the American Association of Physicists in Medicine," *Int. J. Radiat. Oncol. Biol. Phys.*, vol. 58, no. 5, pp. 1616-1634, April 2004, doi: 10.1016/j.ijrobp.2003.12.008.

[2] R. D. Timmerman and L. Xing, *Image-guided and adaptive radiation therapy*. Lippincott Williams & Wilkins, 2012.

[3] A. Fu, B. Ungun, L. Xing, and S. Boyd, "A convex optimization approach to radiation treatment planning with dose constraints," *Optim. Eng.*, vol. 20, no. 1, pp. 277-300, March 2019, doi: 10.1007/s11081-018-9409-2.

[4] H.-P. Wieser et al., "Development of the open-source dose calculation and optimization toolkit matRad," *Med. Phys.*, vol. 44, no. 6, pp. 2556-2568, 2017, doi: 10.1002/mp.12251.

[5] K. Otto, "Volumetric modulated arc therapy: IMRT in a single gantry arc.," *Med. Phys.*, vol. 35, no. 1, pp. 310-317, January 2008, doi: 10.1118/1.2818738.

[6] M. Rao et al., "Comparison of Elekta VMAT with helical tomotherapy and fixed field IMRT: plan quality, delivery efficiency and accuracy.," *Med. Phys.*, vol. 37, no. 3, pp. 1350-1359, March 2010, doi: 10.1118/1.3326965.

[7] W. F. A. R. Verbakel, J. P. Cuijpers, D. Hoffmans, M. Bieker, B. J. Slotman, and S. Senan, "Volumetric intensity-modulated arc therapy vs. conventional IMRT in head-and-neck cancer: a comparative planning and dosimetric study.," *Int. J. Radiat. Oncol. Biol. Phys.*, vol. 74, no. 1, pp. 252-259, May 2009, doi: 10.1016/j.ijrobp.2008.12.033.

[8] D. Wolff et al., "Volumetric modulated arc therapy (VMAT) vs. serial tomotherapy, step-and-shoot IMRT and 3D-conformal RT for treatment of prostate cancer.," *Radiother. Oncol. J. Eur. Soc. Ther. Radiol. Oncol.*, vol. 93, no. 2, pp. 226-233, November 2009, doi: 10.1016/j.radonc.2009.08.011.

[9] E. M. QUAN et al., "A comprehensive comparison of IMRT and VMAT plan quality for prostate cancer treatment," *Int. J. Radiat Oncol. Biol. Phys.*, vol. 83, no. 4, pp. 1169-1178, July 2012, doi: 10.1016/j.ijrobp.2011.09.015.

[10] S. A. Rosenthal et al., "Comparison of Volumetric Modulated Arc Therapy (VMAT) vs. Fixed Field Intensity Modulated Radiation Therapy (IMRT) Techniques for the Treatment of Localized Prostate Cancer," *Int. J. Radiat Oncol. Biol. Phys.*, vol. 78, no. 3, p. 5755, November 2010, doi: 10.1016/j.ijrobp.2010.07.1747.

[11] N. Hardcastle, W. A. Tome, K. Foo, A. Miller, M. Carolan, and P. Metcalfe, "Comparison of prostate IMRT and VMAT biologically optimised treatment plans," *Med. Dosim. Off. J. Am. Assoc. Med. Dosim.*, vol. 36, no. 3, pp. 292-298, 2011, doi: 10.1016/j.meddos.2010.06.001.

[12] V. H. Clark, Y. Chen, J. Wilkens, J. R. Alaly, K. Zakaryan, and J. O. Deasy, "IMRT treatment planning for prostate cancer using prioritized prescription optimization and mean-tail-dose functions," *Linear Algebra Its Appl.*, vol. 428, no. 5-6, pp. 1345-1364, March 2008, doi: 10.1016/j.laa.2007.07.026.

[13] C. Shen et al., "Operating a treatment planning system using a deep-reinforcement learning-based virtual treatment planner for prostate cancer intensity-modulated radiation therapy treatment planning," *Med. Phys., March 2020*, doi: 10.1002/mp.14114.

[14] D. Roach et al., "Adapting automated treatment planning configurations across international centres for prostate radiotherapy," *Phys. Imaging Radiat Oncol.*, vol. 10, pp. 7-13, April 2019, doi: 10.1016/j.phro.2019.04.007.

[15] B. E. Nelms et al., "Variation in external beam treatment plan quality: An inter-institutional study of planners and planning systems," *Pract. Radiat Oncol.*, vol. 2, no. 4, pp. 296-305, October 2012, doi: 10.1016/j.prro.2011.11.012.

[16] S. L. Berry, A. Boczkowski, R. Ma, J. Mechalakos, and M. Hunt, "Interobserver variability in radiation therapy plan output: Results of a single-institution study," *Pract. Radiat. Oncol.*, vol. 6, no. 6, pp. 442-449, November 2016, doi: 10.1016/j.prro.2016.04.005.

[17] V. Batumalai, M. G. Jameson, D. F. Forstner, P. Vial, and L. C. Holloway, "How important is dosimetrist experience for intensity modulated radiation therapy? A comparative analysis of a head and neck case," *Pract. Radiat. Oncol.*, vol. 3, no. 3, pp. e99-e106, July 2013, doi: 10.1016/j.prro.2012.06.009.

[18] K. L. Moore, R. S. Brame, D. A. Low, and S. Mutic, "Quantitative Metrics for Assessing Plan Quality," *Semin. Radiat. Oncol.*, vol. 22, no. 1, pp. 62-69, January 2012, doi: 10.1016/j.semradonc.2011.09.005.

[19] L. Xing, J. G. Li, S. Donaldson, Q. T. Le, and A. L. Boyer, "Optimization of importance factors in inverse planning," *Phys. Med. Biol.*, vol. 44, no. 10, pp. 2525-2536, September 1999, doi: 10.1088/0031-9155/44/10/311.

[20] D. L. Craft, T. F. Halabi, H. A. Shih, and T. R. Bortfeld, "Approximating convex Pareto surfaces in multiobjective radiotherapy planning," *Med. Phys.*, vol. 33, no. 9, pp. 3399-3407, 2006, doi: 10.1118/1.2335486.

[21] D. L. Craft, T. S. Hong, H. A. Shih, and T. R. Bortfeld, "Improved Planning Time and Plan Quality Through Multicriteria Optimization for Intensity-modulated Radiotherapy," *Int. J. Radiat. Oncol. Biol. Phys.*, vol. 82, no. 1, pp. e83-e90, January 2012, doi: 10.1016/j.ijrobp.2010.12.007.

[22] M. Hussein, B. J. M. Heijmen, D. Verellen, and A. Nisbet, "Automation in intensity modulated radiotherapy treatment planning—a review of recent innovations," *Br. J. Radiol.*, vol. 91, no. 1092, p. 20180270, September 2018, doi: 10.1259/bjr.20180270.

[23] Y. Ge and Q. J. Wu, "Knowledge-based planning for intensity-modulated radiation therapy: A review of data-driven approaches," *Med. Phys.*, vol. 46, no. 6, pp. 2760-2775, June 2019, doi: 10.1002/mp.13526.

[24] M. Ma, N. Kovalchuk, M. K. Buyyounouski, L. Xing, and Y. Yang, "Incorporating dosimetric features into the prediction of 3D VMAT dose distributions using deep convolutional neural network," *Phys. Med. Biol.*, vol. 64, no. 12, p. 125017, June 2019, doi: 10.1088/1361-6560/ab2146.

[25] A. Fogliata et al., "On the pre-clinical validation of a commercial model-based optimisation engine: Application to volumetric modulated arc therapy for patients with lung or prostate cancer," *Radiother. Oncol.*, vol. 113, no. 3, pp. 385-391, December 2014, doi: 10.1016/j.radonc.2014.11.009.

[26] M. M. Korani, P. Dong, and L. Xing, "MO-G-201-03: Deep-Learning Based Prediction of Achievable Dose for Personalizing Inverse Treatment Planning," *Med. Phys.*, vol. 43, no. 6 Part 32, pp. 3724-3724, 2016, doi: 10.1118/1.4957369.

[27] I. Hazell et al., "Automatic planning of head and neck treatment plans," *J. Appl. Clin. Med. Phys.*, vol. 17, no. 1, pp. 272-282, January 2016, doi: 10.1120/jacmp.v17i1.5901.

[28] C. R. Hansen et al., "Automatic treatment planning improves the clinical quality of head and neck cancer treatment plans," *Clin. Transl. Radiat. Oncol.*, vol. 1, pp. 2-8, September 2016, doi: 10.1016/j.ctro.2016.08.001.

[29] C. R. Hansen et al., "Automatic treatment planning facilitates fast generation of high-quality treatment plans for esophageal cancer," *Acta Oncol.*, vol. 56, no. 11, pp. 1495-1500, November 2017, doi: 10.1080/0284186X.2017.1349928.

[30] Y. Yang, K. Shao, J. Zhang, M. Chen, Y. Chen, and G. Shan, "Automatic Planning for Nasopharyngeal Carcinoma Based on Progressive Optimization in RayStation Treatment Planning System:" *Technol. Cancer Res. Treat.*, June 2020, doi: 10.1177/1533033820915710.

[31] D. Craft and T. Bortfeld, "How many plans are needed in an IMRT multi-objective plan database?," *Phys. Med. Biol.*, vol. 53, no. 11, pp. 2785-2796, May 2008, doi: 10.1088/0031-9155/53/11/002.

[16] D. L. Craft, T. S. Hong, H. A. Shih, and T. R. Bortfeld, "Improved Planning Time and Plan Quality Through Multicriteria Optimization for Intensity-modulated Radiotherapy," *Int J Radiat Oncol Biol Phys*, vol. 82, no. 1, pp. e83-e90, January 2012, doi: 10.1016/j.ijrobp.2010.12.007.

[33] J. J. Wilkens, J. R. Alaly, K. Zakarian, W. L. Thorstad, and J. O. Deasy, "IMRT treatment planning based on prioritizing prescription goals," *Phys. Med. Biol.*, vol. 52, no. 6, pp. 1675-1692, March 2007, doi: 10.1088/0031-9155/52/6/009.

[34] S. Breedveld, P. R. M. Storchi, M. Keijzer, A. W. Heemink, and B. J. M. Heijmen, "A novel approach to multi-criteria inverse planning for IMRT," *Phys. Med. Biol.*, vol. 52, no. 20, pp. 6339-6353, October 2007, doi: 10.1088/0031-9155/52/20/016.

[35] S. E, L. M, X. L, and B. D, "Multiobjective evolutionary optimization of the number of beams, their orientations and weights for intensity-modulated radiation therapy," *Phys. Med. Biol.*, vol. 49, no. 5, pp. 747-770, March 2004, doi: 10.1088/0031-9155/49/5/007.

[36] C. S. Mayo et al., "Incorporating big data into treatment plan evaluation: Development of statistical DVH metrics and visualization dashboards," *Adv. Radiat. Oncol.*, vol. 2, no. 3, pp. 503-514, September 2017, doi: 10.1016/j.adro.2017.04.005.

[37] S. Shalev, D. Viggars, M. Carey, and P. Hahn, "The objective evaluation of alternative treatment plans: II. Score functions," *Int. J. Radiat. Oncol.*, vol. 20, no. 5, pp. 1067-1073, May 1991, doi: 10.1016/0360-3016(91)90206-J.

[38] M. J. Chen et al., "Intensity modulated radiotherapy for localized prostate cancer: rigid compliance to dose-volume constraints as a warranty of acceptable toxicity?," *Radiat. Oncol.*, vol. 2, no. 1, p. 6, January 2007, doi: 10.1186/1748-717X-2-6.

[39] S. Cilia et al., "Template-based automation of treatment planning in advanced radiotherapy: a comprehensive dosimetric and clinical evaluation," *Sci. Rep.*, vol. 10, no. 1, Art. no. 1, January 2020, doi: 10.1038/s41598-019-56966-y.

[40] R. L.-F. Burden Douglas J., *Numerical analysis*. Boston: PWS Publishing Company, 1985.

[41] J. A. Nelder and R. Mead, "A Simplex Method for Function Minimization," *Comput. J.*, vol. 7, no. 4, pp. 308-313, January 1965, doi: 10.1093/comjnl/7.4.308.

[42] A. Pyakuryal, W. K. Myint, M. Gopalakrishnan, S. Jang, J. A. Logemann, and B. B. Mittal, "A computational tool for the efficient analysis of dose-volume histograms for radiation therapy treatment plans," *J. Appl. Clin. Med. Phys.*, vol. 11, no. 1, pp. 137-157, 2010, doi: 10.1120/jacmp.v11i1.3013.

[43] T. Ventura, M. do C. Lopes, B. C. Ferreira, and L. Khouri, "SPIDERplan: A tool to support decision-making in radiation therapy treatment plan assessment," *Rep. Pract. Oncol. Radiother.*, vol. 21, no. 6, pp. 508-516, November 2016, doi: 10.1016/j.rpor.2016.07.002.

[44] T. Cao, Z. Dai, Z. Ding, W. Li, and H. Quan, "Analysis of different evaluation indexes for prostate stereotactic body radiation therapy plans: conformity index, homogeneity index and gradient index," *Precis. Radiat. Oncol.*, vol. 3, no. 3, pp. 72-79, 2019, doi: 10.1002/pro6.1072.

[45] T. Kataria, K. Sharma, V. Subramani, K. P. Karrthick, and S. S. Bisht, "Homogeneity Index: An objective tool for assessment of conformal radiation treatments," *J. Med. Phys. Assoc. Med. Phys. India*, vol. 37, no. 4, pp. 207-213, 2012, doi: 10.4103/0971-6203.103606.

[46] A. van't Riet, A. C. Mak, M. A. Moerland, L. H. Elders, and W. van der Zee, "A conformation number to quantify the degree of conformality in brachytherapy and external beam irradiation: application to the prostate," *Int. J. Radiat. Oncol. Biol. Phys.*, vol. 37, no. 3, pp. 731-736, February 1997, doi: 10.1016/s0360-3016(96)00601-3.

[47] V. A. Semenenko, B. Reitz, E. Day, X. S. Qi, M. Miften, and X. A. Li, "Evaluation of a commercial biologically based IMRT treatment planning system," *Med. Phys.*, vol. 35, no. 12, pp. 5851-5860, December 2008, doi: 10.1118/1.3013556.

[48] I. Paddick, "A simple scoring ratio to index the conformity of radiosurgical treatment plans. Technical note," *J. Neurosurg.*, vol. 93 Suppl 3, pp. 219-222, December 2000, doi: 10.3171/jns.2000.93.supplement.

[49] A. Wachter and L. T. Biegler, "On the implementation of an interior-point filter line-search algorithm for large-scale nonlinear programming," *Math. Program.*, vol. 106, no. 1, pp. 25-57, March 2006, doi: 10.1007/s10107-004-0559-y.

[50] S. Holm, "A Simple Sequentially Rejective Multiple Test Procedure," *Scand. J. Stat.*, vol. 6, no. 2, pp. 65-70, 1979.

[51] L. Xing, J. G. Li, A. Pugachev, Q. T. Le, and A. L. Boyer, "Estimation theory and model parameter selection for therapeutic treatment plan optimization," *Med. Phys.*, vol. 26, no. 11, pp. 2348-2358, 1999, doi: 10.1118/1.598749.

[52] G. Kalantzis and A. Apte, "A Novel Reduced-Order Prioritized Optimization Method for Radiation Therapy Treatment Planning," *IEEE Trans. Biomed. Eng.*, vol. 61, no. 4, pp. 1062-1070, April 2014, doi: 10.1109/TBME.2013.2293779.

[53] K.-W. Jee, D. L. McShan, and B. A. Fraass, "Lexicographic ordering: intuitive multicriteria optimization for IMRT," *Phys. Med. Biol.*, vol. 52, no. 7, pp. 1845-1861, April 2007, doi: 10.1088/0031-9155/52/7/006.

[54] K. Y. Bilimoria, A. K. Stewart, D. P. Winchester, and C. Y. Ko, "The National Cancer Data Base: A Powerful Initiative to Improve Cancer Care in the United States," *Ann. Surg. Oncol.*, vol. 15, no. 3, pp. 683-690, March 2008, doi: 10.1245/s10434-007-9747-3.

[55] L. Xing, M. Giger, and J. Min, *Artificial Intelligence Medicine: Technical Basis and Clinical Applications*, 1st ed. St. Louis, Mo.: Elsevier S&T Books.

Bangert M and Oelfke U 2010 Spherical cluster analysis for beam angle optimization in intensity-modulated radiation therapy treatment planning *Phys. Med. Biol.* 55 6023-37

Bangert M, Ziegenhein P and Oelfke U 2013 Comparison of beam angle selection strategies for intracranial IMRT *Med. Phys.* 40 011716

Batumalai V, Jameson M G, Forstner D F, Vial P and Holloway L C 2013 How important is dosimetrist experience for intensity modulated radiation therapy? A comparative analysis of a head and neck case *Pract. Radiat. Oncol.* 3 e99-106

Berry S L, Boczkowski A, Ma R, Mechalakos J and Hunt M 2016 Interobserver variability in radiation therapy plan output: Results of a single-institution study *Pract. Radiat. Oncol.* 6 442-9

Cao T, Dai Z, Ding Z, Li W and Quan H 2019 Analysis of different evaluation indexes for prostate stereotactic body radiation therapy plans: conformity index, homogeneity index and gradient index *Precis. Radiat. Oncol.* 3 72-9

Christiansen E, Heath E and Xu T 2018 Continuous aperture dose calculation and optimization for volumetric modulated arc therapy *Phys. Med. Biol.* 63 21NT01

Clark V H, Chen Y, Wilkens J, Alaly J R, Zakaryan K and Deasy J O 2008 IMRT treatment planning for prostate cancer using prioritized prescription optimization and mean-tail-dose functions *Linear Algebra Its Appl.* 428 1345-64

Crooks S M, Wu X, Takita C, Watzich M and Xing L 2003 Aperture modulated arc therapy *Phys. Med. Biol.* 48 1333-44

Fix M K, Frei D, Volken W, Terribilini D, Mueller S, Elicin O, Hemmatazad H, Aebersold D M and Manser P 2018 Part 1: Optimization and evaluation of dynamic trajectory radiotherapy *Med. Phys.*

Fu A, Ungun B, Xing L and Boyd S 2019 A convex optimization approach to radiation treatment planning with dose constraints *Optim. Eng.* 20 277-300

Galvin J M, Ezzell G, Eisbrauch A, Yu C, Butler B, Xiao Y, Rosen I, Rosenman J, Sharpe M, Xing L, Xia P, Lomax T, Low D A and Palta J 2004 Implementing IMRT in clinical practice: a joint document of the American Society for Therapeutic Radiology and Oncology and the American Association of Physicists in Medicine *Int. J. Radiat. Oncol. Biol. Phys.* 58 1616-34

Hardcastle N, Tomé W A, Foo K, Miller A, Carolan M and Metcalfe P 2011 Comparison of prostate IMRT and VMAT biologically optimised treatment plans *Med. Dosim. Off. J. Am. Assoc. Med. Dosim.* 36 292-8

Hou Q, Wang J, Chen Y and Galvin J M 2003 Beam orientation optimization for IMRT by a hybrid method of the genetic algorithm and the simulated dynamics *Med. Phys.* 30 2360-7

Huang C, Yang Y, Panjwani N, Boyd S and Xing L 2021 Pareto Optimal Projection Search (POPS): Automated Radiation Therapy Treatment Planning by Direct Search of the Pareto Surface *IEEE Trans. Biomed. Eng.* 1-1

Hussein M, Heijmen B J M, Verellen D and Nisbet A 2018 Automation in intensity modulated radiotherapy treatment planning—a review of recent innovations *Br. J. Radiol.* 91 20180270

Kataria T, Sharma K, Subramani V, Karrthick K P and Bisht S S 2012 Homogeneity Index: An objective tool for assessment of conformal radiation treatments *J. Med. Phys. Assoc. Med. Phys. India* 37 207-13

Li R and Xing L 2013 An adaptive planning strategy for station parameter optimized radiation therapy (SPORT): Segmentally boosted VMAT *Med. Phys.* 40 Online: https://www.ncbi.nlm.nih.gov/pmc/articles/PMC3656955/

Li R and Xing L 2011 Bridging the gap between IMRT and VMAT: Dense angularly sampled and sparse intensity modulated radiation therapy *Med. Phys.* 38 4912-9

Li Y, Yao D, Yao J and Chen W 2005 A particle swarm optimization algorithm for beam angle selection in intensity-modulated radiotherapy planning *Phys. Med. Biol.* 50 3491-514

Li Y, Yao J and Yao D 2004 Automatic beam angle selection in IMRT planning using genetic algorithm *Phys. Med. Biol.* 49 1915-32

MacDonald R L and Thomas C G 2015 Dynamic trajectory-based couch motion for improvement of radiation therapy trajectories in cranial SRT *Med. Phys.* 42 2317-25

Moore K L, Brame R S, Low D A and Mutic S 2012 Quantitative Metrics for Assessing Plan Quality *Semin. Radiat. Oncol.* 22 62-9

Nelder J A and Mead R 1965 A Simplex Method for Function Minimization *Comput. J.* 7 308-13

Nelms B E, Robinson G, Markham J, Velasco K, Boyd S, Narayan S, Wheeler J and Sobczak M L 2012 Variation in external beam treatment plan quality: An inter-institutional study of planners and planning systems *Pract. Radiat. Oncol.* 2 296-305

Otto K 2008 Volumetric modulated arc therapy: IMRT in a single gantry arc. *Med. Phys.* 35 310-7

Paddick I 2000 A simple scoring ratio to index the conformity of radiosurgical treatment plans. Technical note *J. Neurosurg.* 93 Suppl 3 219-22

Papp D, Bortfeld T and Unkelbach J 2015 A modular approach to intensity-modulated arc therapy optimization with noncoplanar trajectories *Phys. Med. Biol.* 60 5179-98

Papp D and Unkelbach J 2014 Direct leaf trajectory optimization for volumetric modulated arc therapy planning with sliding window delivery *Med. Phys.* 41 011701

Pugachev A, Li J G, Boyer A L, Hancock S L, Le Q-T, Donaldson S S and Xing L 2001 Role of beam orientation optimization in intensity-modulated radiation therapy *Int. J. Radiat. Oncol. Biol. Phys.* 50 551-60

Pugachev A and Xing L 2002 Incorporating prior knowledge into beam orientation optimization in IMRT *Int. J. Radiat. Oncol. Biol. Phys.* 54 1565-74

Pyakuryal A, Myint W K, Gopalakrishnan M, Jang S, Logemann J A and Mittal B B 2010 A computational tool for the efficient analysis of dose-volume histograms for radiation therapy treatment plans *J. Appl. Clin. Med. Phys.* 11 137-57

QUAN E M, LI X, LI Y, WANG X, KUDCHADKER R J, JOHNSON J L, KUBAN D A, LEE A K and ZHANG X 2012 A comprehensive comparison of IMRT and VMAT plan quality for prostate cancer treatment *Int. J. Radiat. Oncol. Biol. Phys.* 83 1169-78

Rao M, Yang W, Chen F, Sheng K, Ye J, Mehta V, Shepard D and Cao D 2010 Comparison of Elekta VMAT with helical tomotherapy and fixed field IMRT: plan quality, delivery efficiency and accuracy. *Med. Phys.* 37 1350-9 van't Riet A, Mak A C, Moerland M A, Elders L H and van der Zee W 1997 A conformation number to quantify the degree of conformality in brachytherapy and external beam irradiation: application to the prostate *Int. J. Radiat. Oncol. Biol. Phys.* 37 731-6

Roach D, Wortel G, Ochoa C, Jensen H R, Damen E, Vial P, Janssen T and Hansen C R 2019 Adapting automated treatment planning configurations across international centres for prostate radiotherapy *Phys. Imaging Radiat. Oncol.* 10 7-13

Rosenthal S A, Wu C, Mangat J K, Tunnicliff C J, Chang G C, Dutton S C, Goldsmith B J, Leibenhaut M H, Logsdon M D and Asche D R 2010 Comparison of Volumetric Modulated Arc Therapy (VMAT) vs. Fixed Field Intensity Modulated Radiation Therapy (IMRT) Techniques for the Treatment of Localized Prostate Cancer *Int. J. Radiat. Oncol. Biol. Phys.* 78 5755

Semenenko V A, Reitz B, Day E, Qi X S, Miften M and Li X A 2008 Evaluation of a commercial biologically based IMRT treatment planning system *Med. Phys.* 35 5851-60

Shen C, Nguyen D, Chen L, Gonzalez Y, McBeth R, Qin N, Jiang S B and Jia X 2020 Operating a treatment planning system using a deep-reinforcement learning-based virtual treatment planner for prostate cancer intensity-modulated radiation therapy treatment planning *Med. Phys.*

Smyth G, Bamber J C, Evans P M and Bedford J L 2013 Trajectory optimization for dynamic couch rotation during volumetric modulated arc radiotherapy *Phys. Med. Biol.* 58 8163-77

Smyth G, Evans P M, Bamber J C and Bedford J L 2019 Recent developments in non-coplanar radiotherapy *Br. J. Radiol.* 92 Online: https://www.ncbi.nlm.nih.gov/pmc/articles/PMC6580906/Stein J, Mohan R, Wang X-H, Bortfeld T, Wu Q, Preiser K, Ling C C and Schlegel W 1997 Number and orientations of beams in intensity-modulated radiation treatments *Med. Phys.* 24 149-60

Timmerman R D and Xing L 2012 *Image-guided and adaptive radiation therapy* (Lippincott Williams & Wilkins)

Unkelbach J, Bortfeld T, Craft D, Alber M, Bangert M, Bokrantz R, Chen D, Li R, Xing L, Men C, Nill S, Papp D, Romeijn E and Salari E 2015 Optimization approaches to volumetric modulated arc therapy planning *Med. Phys.* 42 1367-77

Ventura T, Lopes M do C, Ferreira B C and Khouri L 2016 SPIDERplan: A tool to support decision-making in radiation therapy treatment plan assessment *Rep. Pract. Oncol. Radiother.* 21 508-16

Verbakel W F A R, Cuijpers J P, Hoffmans D, Bieker M, Slotman B J and Senan S 2009 Volumetric intensity-modulated arc therapy vs. conventional IMRT in head-and-neck cancer: a comparative planning and dosimetric study. *Int. J. Radiat. Oncol. Biol. Phys.* 74 252-9

Wang C, Dai J and Hu Y 2003 Optimization of beam orientations and beam weights for conformal radiotherapy using mixed integer programming *Phys. Med. Biol.* 48 4065-76

Wieser H-P, Cisternas E, Wahl N, Ulrich S, Stadler A, Mescher H, Müller L-R, Klinge T, Gabrys H, Burigo L, Mairani A, Ecker S, Ackermann B, Ellerbrock M, Parodi K, Jäkel O and Bangert M 2017 Development of the open-source dose calculation and optimization toolkit matRad *Med. Phys.* 44 2556-68

Wolff D, Stieler F, Welzel G, Lorenz F, Abo-Madyan Y, Mai S, Herskind C, Polednik M, Steil V, Wenz F and Lohr F 2009 Volumetric modulated arc therapy (VMAT) vs. serial tomotherapy, step-and-shoot IMRT and 3D-conformal RT for treatment of prostate cancer. *Radiother. Oncol. J. Eur. Soc. Ther. Radiol. Oncol.* 93 226-33

Woudstra E and Storchi P R M 2000 Constrained treatment planning using sequential beam selection *Phys. Med. Biol.* 45 2133-49

Wu X, Zhu Y, Dai J and Wang Z 2000 Selection and determination of beam weights based on genetic algorithms for conformal radiotherapy treatment planning *Phys. Med. Biol.* 45 2547-58

Xing L, Li J G, Donaldson S, Le Q T and Boyer A L 1999 Optimization of importance factors in inverse planning *Phys. Med. Biol.* 44 2525-36

Xing L and Li R 2014 Inverse planning in the age of digital LINACs: station parameter optimized radiation therapy (SPORT) *J. Phys. Conf. Ser.* 489 012065

Yang Y, Shao K, Zhang J, Chen M, Chen Y and Shan G 2020 Automatic Planning for Nasopharyngeal Carcinoma Based on Progressive Optimization in RayStation Treatment Planning System: *Technol. Cancer Res. Treat.* Online: https://journals.sagepub.com/doi/10.1177/1533033820915710

Yang Y, Zhang P, Happersett L, Xiong J, Yang J, Chan M, Beal K, Mageras G and Hunt M 2011 Choreographing Couch and Collimator in Volumetric Modulated Arc Therapy *Int. J. Radiat. Oncol. Biol. Phys.* 80 1238-47

Yu C X 1995 Intensity-modulated arc therapy with dynamic multileaf collimation: an alternative to tomotherapy *Phys. Med. Biol.* 40 1435-49

The invention claimed is:

1. A method for radiation therapy treatment planning, the method comprising:
    a) defining a decision variable search space by projecting an initial seed point onto a pareto front, where the pareto front and the decision variable search space are defined in a coordinate space;
    b) projecting search points in the decision variable search space to the pareto front using a one-dimensional search algorithm to produce projected points on the pareto front;
    c) updating the search points by performing a gradient-free optimization that evaluates a treatment planning scoring function at the projected points on the pareto front; and
    d) repeating steps (b), (c) to search within the decision variable search space until a convergence criterion is satisfied, thereby producing a pareto optimal and clinically acceptable treatment plan.

2. The method of claim 1, further comprising performing beam angle optimization using combinatorial optimization.

3. The method of claim 2, wherein the beam angle optimization is non-coplanar.

4. The method of claim 2, wherein the beam angle optimization is coplanar.

* * * * *